United States Patent
Nakamura et al.

(10) Patent No.: US 7,256,279 B2
(45) Date of Patent: Aug. 14, 2007

(54) PROTEIN HAVING RIBONUCLEOTIDE REDUCTASE ACTIVITY AND DNA THEREOF

(75) Inventors: Yusuke Nakamura, Kanagawa (JP); Hirofumi Arakawa, Tokyo (JP); Hiroshi Tanaka, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 465 days.

(21) Appl. No.: 10/698,228

(22) Filed: Oct. 30, 2003

(65) Prior Publication Data

US 2004/0072253 A1 Apr. 15, 2004

Related U.S. Application Data

(62) Division of application No. 10/019,733, filed as application No. PCT/JP00/04189 on Jun. 27, 2000, now Pat. No. 6,682,917.

(30) Foreign Application Priority Data

| Jun. 28, 1999 | (JP) | ............................. 1999-181131 |
| Jul. 6, 1999 | (JP) | ............................. 1999-192391 |
| Jan. 21, 2000 | (JP) | ............................. 2000-017770 |

(51) Int. Cl.
*C07H 21/04* (2006.01)
*C12N 1/20* (2006.01)
*C12N 9/02* (2006.01)
*C12N 15/00* (2006.01)
*C12P 21/00* (2006.01)

(52) U.S. Cl. .................... 536/23.2; 435/70.1; 435/71.1; 435/189; 435/252.3; 435/252.33; 435/325

(58) Field of Classification Search ..................... None
See application file for complete search history.

(56) References Cited

U.S. PATENT DOCUMENTS 5,891,621 A 4/1999 Chabin et al. .................. 435/4

FOREIGN PATENT DOCUMENTS

| EP | 0726 277 A2 | 8/1996 |
| JP | A-10-14582 | 1/1998 |
| WO | WO99/06552 | 11/1999 |
| WO | WO 00/15799 | 3/2000 |

OTHER PUBLICATIONS

N_Geneseq_Dec. 16, 2004 Database Accession No. AAA12411 Jul. 25, 2000 from WO200015799 Tang et al. Mar. 23, 2000 priority 60/128,660 filed Apr. 8, 1999. Alignment with Seq. Id No. 1.*
N_Geneseq_Dec. 16, 2004 Database Accession No. AAA12411 Jul. 25, 2000 from WO200015799 Tang et al. Mar. 23, 2000 priority 60/128,660 filed Apr. 8, 1999. Alignment with Seq. Id No. 2.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Fernandez-Trigo et al, Prognostic implications of chemoresistance-sensitivity assays for colorectal and apprendiceal cancer. Am J Clin Oncol. Oct. 1995;18(5):454-60.*
European Patent Office Communication mailed Apr. 19, 2004 (3 pp.) for corresponding application No. 00940840.2.
Pavloff, Nadine, et al "Sequence Analysis of the Large and Small Subunits of Human Ribonucleotide Reductase", *DNA Sequence—J. DNA Sequencing and Mapping*, (1992), vol. 2, No. 4-pp. 227-234. GenBank Accession No. X59618).
Reichard, Peter, "From RNA to DNA, Why So Many Reibonucleotide Reductases?", *Science*(1993) vol. 260, No. 5115, 1773-1777.
Tanaka, Hiroshi, et al., "A Ribonucleotide Reductase Gene Involved In a p53-Dependent Cell-Cycle Checkpoint for DNA Damage", *Nature*, (2000), vol. 404, No. 6773, p. 42-49.
Ansorge et al, T46249 hypothetical protein DKFZp761E1312.1. Feb. 4, 2000. EMBL Acc# AL137348. Alignment with Seq. Id No. 1.
Pavloff et al, Ribonucleoside-diphosphate reductuase M2 chain. Jul. 1, 1993. SwissProt Acc# P31350. Alignment with Seq Id No. 1.
Duclert et al, Human secreted protein encoded by 5'Est Seq Id No.: 88. ID# AAY13074 from WO9906552-A2. 22=Jun. 1999. Alignment with Seq. Id No. 1.
Yumi et al, Ribonucleotide Reductase Abstract from JP10014582A. Jan. 20, 1998 and attached IDS for PCT/JP00/04189.

* cited by examiner

*Primary Examiner*—Sheridan Swope
(74) *Attorney, Agent, or Firm*—Edwards Angell Palmer & Dodge LLP; David G. Conlin; Mark D. Russett

(57) ABSTRACT

A protein having ribonucleotide reductase activity, DNA encoding the protein, antibodies to these and the like are disclosed. The protein, DNA and antibodies are useful in the prevention, treatment and diagnosis, etc. of cancer.

6 Claims, 10 Drawing Sheets

FIG. 1A

Range : 1 - 1053   Mode : Normal
Codon Table : Universal

```
              9          18          27          36          45          54
5' ATG GGC GAC CCG GAA AGG CCG GAA GCG GCC GGG CTG GAT CAG GAT GAG AGA TCA
   --- --- --- --- --- --- --- --- --- --- --- --- --- --- --- --- --- ---
   Met Gly Asp Pro Glu Arg Pro Glu Ala Ala Gly Leu Asp Gln Asp Glu Arg Ser 63         72          81          90          99         108
   TCT TCA GAC ACC AAC GAA AGT GAA ATA AAG TCA AAT GAA GAG CCA CTC CTA AGA
   --- --- --- --- --- --- --- --- --- --- --- --- --- --- --- --- --- ---
   Ser Ser Asp Thr Asn Glu Ser Glu Ile Lys Ser Asn Glu Glu Pro Leu Leu Arg 117        126         135         144         153        162
   AAG AGT TCT CGC CGG TTT GTC ATC TTT CCA ATC CAG TAC CCT GAT ATT TGG AAA
   --- --- --- --- --- --- --- --- --- --- --- --- --- --- --- --- --- ---
   Lys Ser Ser Arg Arg Phe Val Ile Phe Pro Ile Gln Tyr Pro Asp Ile Trp Lys 171        180         189         198         207        216
   ATG TAT AAA CAG GCA CAG GCT TCC TTC TGG ACA GCA GAA GAG GTC GAC TTA TCA
   --- --- --- --- --- --- --- --- --- --- --- --- --- --- --- --- --- ---
   Met Tyr Lys Gln Ala Gln Ala Ser Phe Trp Thr Ala Glu Glu Val Asp Leu Ser 225        234         243         252         261        270
   AAG GAT CTC CCT CAC TGG AAC AAG CTT AAA GCA GAT GAG AAG TAC TTC ATC TCT
   --- --- --- --- --- --- --- --- --- --- --- --- --- --- --- --- --- ---
   Lys Asp Leu Pro His Trp Asn Lys Leu Lys Ala Asp Glu Lys Tyr Phe Ile Ser 279        288         297         306         315        324
   CAC ATC TTA GCC TTT TTT GCA GCC AGT GAT GGA ATT GTA AAT GAA AAT TTG GTG
   --- --- --- --- --- --- --- --- --- --- --- --- --- --- --- --- --- ---
   His Ile Leu Ala Phe Phe Ala Ala Ser Asp Gly Ile Val Asn Glu Asn Leu Val 333        342         351         360         369        378
   GAG CGC TTT AGT CAG GAG GTG CAG GTT CCA GAG GCT CGC TGT TTC TAT GGC TTT
   --- --- --- --- --- --- --- --- --- --- --- --- --- --- --- --- --- ---
   Glu Arg Phe Ser Gln Glu Val Gln Val Pro Glu Ala Arg Cys Phe Tyr Gly Phe 387        396         405         414         423        432
   CAA ATT CTC ATC GAG AAT GTT CAC TCA GAG ATG TAC AGT TTG CTG ATA GAC ACT
   --- --- --- --- --- --- --- --- --- --- --- --- --- --- --- --- --- ---
   Gln Ile Leu Ile Glu Asn Val His Ser Glu Met Tyr Ser Leu Leu Ile Asp Thr
```

FIG. 1B

```
      441         450         459         468         477         486
TAC ATC AGA GAT CCC AAG AAA AGG GAA TTT TTA TTT AAT GCA ATT GAA ACC ATG
--- --- --- --- --- --- --- --- --- --- --- --- --- --- --- --- --- ---
Tyr Ile Arg Asp Pro Lys Lys Arg Glu Phe Leu Phe Asn Ala Ile Glu Thr Met 495         504         513         522         531         540
CCC TAT GTT AAG AAA AAA GCA GAT TGG GCC TTG CGA TGG ATA GCA GAT AGA AAA
--- --- --- --- --- --- --- --- --- --- --- --- --- --- --- --- --- ---
Pro Tyr Val Lys Lys Lys Ala Asp Trp Ala Leu Arg Trp Ile Ala Asp Arg Lys 549         558         567         576         585         594
TCT ACT TTT GGG GAA AGA GTG GTG GCC TTT GCT GCT GTA GAA GGA GTT TTC TTC
--- --- --- --- --- --- --- --- --- --- --- --- --- --- --- --- --- ---
Ser Thr Phe Gly Glu Arg Val Val Ala Phe Ala Ala Val Glu Gly Val Phe Phe
      603         612         621         630         639         648
TCA GGA TCT TTT GCT GCT ATA TTC TGG CTA AAG AAG AGA GGT CTT ATG CCA GGA
--- --- --- --- --- --- --- --- --- --- --- --- --- --- --- --- --- ---
Ser Gly Ser Phe Ala Ala Ile Phe Trp Leu Lys Lys Arg Gly Leu Met Pro Gly 657         666         675         684         693         702
CTC ACT TTT TCC AAT GAA CTC ATC AGC AGA GAT GAA GGA CTT CAC TGT GAC TTT
--- --- --- --- --- --- --- --- --- --- --- --- --- --- --- --- --- ---
Leu Thr Phe Ser Asn Glu Leu Ile Ser Arg Asp Glu Gly Leu His Cys Asp Phe 711         720         729         738         747         756
GCT TGC CTG ATG TTC CAA TAC TTA GTA AAT AAG CCT TCA GAA GAA AGG GTC AGG
--- --- --- --- --- --- --- --- --- --- --- --- --- --- --- --- --- ---
Ala Cys Leu Met Phe Gln Tyr Leu Val Asn Lys Pro Ser Glu Glu Arg Val Arg 765         774         783         792         801         810
GAG ATC ATT GTT GAT GCT GTC AAA ATT GAG CAG GAG TTT TTA ACA GAA GCC TTG
--- --- --- --- --- --- --- --- --- --- --- --- --- --- --- --- --- ---
Glu Ile Ile Val Asp Ala Val Lys Ile Glu Gln Glu Phe Leu Thr Glu Ala Leu 819         828         837         846         855         864
CCA GTT GGC CTC ATT GGA ATG AAT TGC ATT TTG ATG AAA CAG TAC ATT GAG TTT
--- --- --- --- --- --- --- --- --- --- --- --- --- --- --- --- --- ---
Pro Val Gly Leu Ile Gly Met Asn Cys Ile Leu Met Lys Gln Tyr Ile Glu Phe 873         882         891         900         909         918
GTA GCT GAC AGA TTA CTT GTG GAA CTT GGA TTC TCA AAG GTT TTT CAG GCA GAA
--- --- --- --- --- --- --- --- --- --- --- --- --- --- --- --- --- ---
Val Ala Asp Arg Leu Leu Val Glu Leu Gly Phe Ser Lys Val Phe Gln Ala Glu
```

FIG. 1C

```
        927         936         945         954         963         972
AAT CCT TTT GAT TTT ATG GAA AAC ATT TCT TTA GAA GGA AAA ACA AAT TTC TTT
--- --- --- --- --- --- --- --- --- --- --- --- --- --- --- --- --- ---
Asn Pro Phe Asp Phe Met Glu Asn Ile Ser Leu Glu Gly Lys Thr Asn Phe Phe 981         990         999        1008        1017        1026
GAG AAA CGA GTT TCA GAG TAT CAG CGT TTT GCA GTT ATG GCA GAA ACC ACA GAT
--- --- --- --- --- --- --- --- --- --- --- --- --- --- --- --- --- ---
Glu Lys Arg Val Ser Glu Tyr Gln Arg Phe Ala Val Met Ala Glu Thr Thr Asp 1035        1044        1053
AAC GTC TTC ACC TTG GAT GCA GAT TTT 3'
--- --- --- --- --- --- --- --- ---
Asn Val Phe Thr Leu Asp Ala Asp Phe
```

FIG. 2

Lipman-Pearson Protein Alignment
Ktuple: 2; Gap Penalty: 4; Gap Length Penalty: 12

| Seq1(1>351) | Seq2(1>389) | Similarity |
|---|---|---|
| Tp53r2h.pro | R2.pro | Index |
| (15>351) | (53>389) | 80.4 |
| (1>351) | (39>389) | 77.5 |

```
              10        20        30        40        50        60        70        80
TP53R2H  MGDPERPEAAGLDQDERSSSDTNESEIKSNEEPLLRKSSRRFVIFPIQYPDIWKMYKQAQASFWTAEEVDLSKDLPHWNK
           . :.:|   :|.:.:.|:.:.   ::|||||.::|||||||:|.|||:|||:|:||||||||||||||:. ||:.
R2       GTRVLASKTARRIFQEPTEPKTKAAAPGVEDEPLLRENPRRFVIFPIEYHDIWQMYKKAEASFWTAEEVDLSKDIQHWES
           40        50        60        70        80        90        100       110

90        100       110       120       130       140       150       160
TP53R2H  LKADEKYFISHILAFFAASDGIVNENLVERFSQEVQVPEARCFYGFQILIENVHSEMYSLLIDTYIRDPKKREFLFNAIE
         ||::|:|||||:|||||||||||||||||||||||:.||||||||| :||:||||||||||:|||.||||||||
R2       LKPEERYFISHVLAFFAASDGIVNENLVERFSQEVQITEARCFYGFQIAMENIHSEMYSLLIDTYIKDPKEREFLFNAIE
           120       130       140       150       160       170       180       190

170       180       190       200       210       220       230       240
TP53R2H  TMPYVKKKADWALRWIADRKSTFGERVVAFAAVEGVFFSGSFAAIFWLKKRGLMPGLTFSNELISRDEGLHCDFACLMFQ
         |||.|||||||||||:|:. :|:||||||||||||:|||||||:|||||||||||||||||||||||||||||||||||:
R2       TMPCVKKKADWALRWIGDKEATYGERVVAFAAVEGIFFSGSFASIFWLKKRGLMPGLTFSNELISRDEGLHCDFACLMFK
           200       210       220       230       240       250       260       270

250       260       270       280       290       300       310       320
TP53R2H  YLVNKPSEERVREIIVDAVKIEQEFLTEALPVGLIGMNCILMKQYIEFVADRLLVELGFSKVFQAENPFDFMENISLEGK
         .||:|||||||||||::||:||||||||||||| |||||. ||||||||||::|||||||:. |||||||||||||||||
R2       HLVHKPSEERVREIIINAVRIEQEFLTEALPVKLIGMNCTLMKQYIEFVADRLMLELGFSKVFRVENPFDFMENISLEGK
           280       290       300       310       320       330       340       350

330       340       350
TP53R2H  TNFFEKRVSEYQRFAVMAETTDNVFTLDADF
         ||||||||:||||.:||:..|:| |||||||
R2       TNFFEKRVGEYQRMGVMSSPTENSFTLDADF
           360       370       380
```

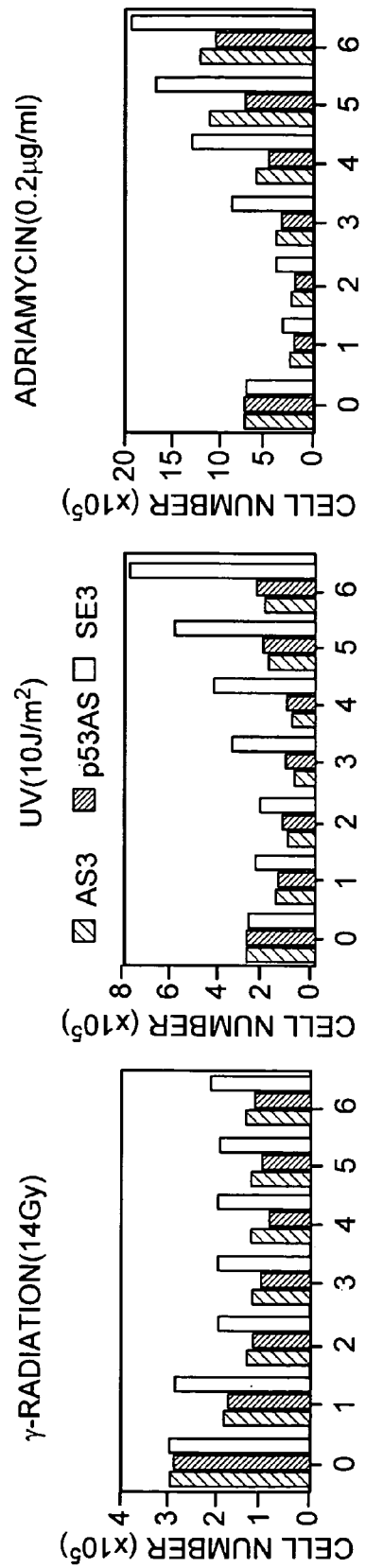

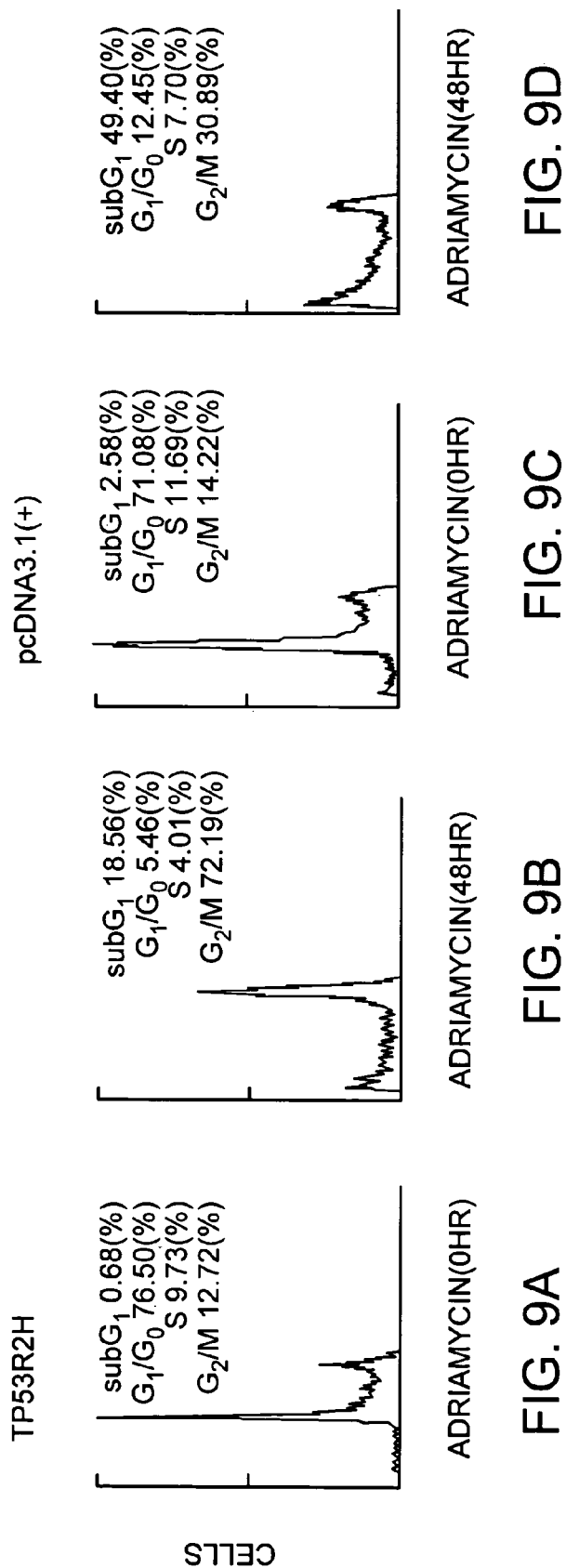

PROTEIN HAVING RIBONUCLEOTIDE REDUCTASE ACTIVITY AND DNA THEREOF

RELATED APPLICATIONS

This application claims priority to U.S. patent application Ser. No. 10/019,733, filed Dec. 28, 2001, now U.S. Pat. No. 6,682,917, which is the U.S. national phase of PCT Application No. PCT/JP00/04189, filed Jun. 27, 2000, which claims priority to Japanese Patent Application Nos. 017770/2000, filed Jan. 21, 2000, 192391/1999, filed Jul. 6, 1999, and 181121/1999, filed Jun. 28, 1999. The entireties of these applications are incorporated herein by reference.

TECHNICAL FIELD

The present invention relates to a novel protein having a homology with ribonucleotide reductase, to the DNA coding the protein and so forth.

BACKGROUND ART

Recent developments of research have proven that cancer is a genetic disease in which multiple genetic mutations accumulate in somatic cells, resulting in uncontrolled cell growth. p53 is the tumor suppressor gene in which abnormalities have been found most frequently in human cancers, and has been clarified to have a variety of physiological functions including induction of G1 arrest and apoptosis, and checkpoint control when DNA is damaged. It is thought that these functions are exercised when p53 acts as a transcription factor to control the expression of the target gene. It is suggested that p53 abnormalities are associated with cancer malignancy, resistance to anti-cancer agents and radiation therapy, metastasis and vascularization (*The New England Journal of Medicine* Vol. 329 p. 1318 (1993), etc.).

Ribonucleotide reductase is a rate-limiting enzyme, which converts ribonucleotides to their corresponding deoxyribonucleotides and supplies them for purposes of DNA synthesis (*Science* Vol. 260 p. 1773 (1993)). This enzyme is a heterodimer comprising a large subunit (R1) and a small subunit (R2), with both R1 and R2 (National Center for Biotechnology Information GenBank Accession No. X59618) consisting of homodimers. Enzyme activity is controlled by the amount of R2. The amount of R2 is controlled depending on the cell cycle, with the most being highly expressed during the S period. Ribonucleotide reductase has been well studied in yeasts, and three subunits (RNR1, RNR2, RNR3) are known to exist in yeasts. RNR1 and RNR3 correspond to R1 in mammals and RNR2 to R2 in mammals, and control of RNR1 expression is dependent on cell cycle. It has been reported that when DNA is damaged by irradiation for example, RNR1 expression is not induced, but induction of RNR3 expression increases more than 100 fold (*Genes & Development* Vol. 4 p. 740 (1990)). It has also been reported that expression of R2 is greater in highly malignant cancer cells, which are resistant to anti-cancer agents and radiation therapy (*Biochemistry and Cell Biology* Vol. 68 p. 1364 (1990)).

The TP53R2H gene obtained in the examples below has a ribonucleotide reductase signature sequence, which has high homology with R2 and is conserved among species, and the product of the TP53R2H gene may be involved in supplying deoxyribonucleotide for DNA synthesis. Since expression of TP53R2H is also induced by DNA damage due to anti-cancer agent treatment or irradiation (not the case with R2), it may be involved particularly in supplying deoxyribonucleotides during DNA repair following DNA damage. It can therefore be expected that blocking of TP53R2H in cases of highly malignant cancer with resistance to anti-cancer agents and radiation therapy would be a highly effective treatment with few side-effects. Moreover, because TP53R2H may act as a homodimer (as R2 does), it might be possible to confer a dominant negative effect and suppress the activity of the enzyme by introducing mutated TP53R2H genes or TP53R2H protein into cancer cells, so both mutated TP53R2H genes and TP53R2H protein should be useful as therapeutic agents for highly malignant cancers with resistance to anti-cancer agents and radiation therapy. In addition, investigation of mutations to this gene should be useful in cancer diagnosis and prevention.

DISCLOSURE OF THE INVENTION

As a result of dedicated research, the present inventors succeeded in cloning, from a human muscle-derived cDNA library, cDNA which codes for a novel protein having a homology with ribonucleotide reductase, and perfected the present invention as a result of further study based on these findings.

That is, the present invention relates to:

(1) A protein having the same or substantially the same amino acid sequence as the amino acid sequence represented by SEQ ID NO: 1, or a salt thereof;

(2) The protein according to (1) above, having ribonucleotide reductase activity;

(3) A partial peptide of the protein according to (1) above, or a salt thereof;

(4) DNA comprising DNA having a base sequence encoding the protein according to (1) above or the partial peptide according to (3) above;

(5) DNA according to (4) above, having the base sequence represented by SEQ ID NO: 2;

(6) DNA according to (4) above, having the base sequence represented by SEQ ID NO: 12;

(7) A recombinant vector comprising the DNA according to (4) above;

(8) A transformant transformed by the recombinant vector according to (7) above;

(9) A method for manufacturing the protein or salt thereof according to (1) above or the partial peptide or salt thereof according to (3) above, wherein the transformant according to (8) above is cultured to produce the protein or salt thereof according to (1) above or partial peptide or salt thereof according to (3) above, which is then accumulated and collected;

(10) A pharmaceutical comprising the protein or salt thereof according to (1) above or the partial peptide or salt thereof according to (3) above;

(11) A pharmaceutical comprising the DNA according to (4) above;

(12) An antibody to the protein or salt thereof according to (1) above or the partial peptide or salt thereof according to (3) above;

(13) A diagnostic agent comprising the antibody according to (12) above;

(14) A method for screening a compound or salt thereof which inhibits or activates the enzyme activity of the protein or salt thereof according to (1) above, characterized by the use of the protein or salt thereof according to (1) above or the partial peptide or salt thereof according to (3) above;

(15) A kit for screening a compound or salt thereof which inhibits or activates the enzyme activity of the protein or salt thereof according to (1) above, comprising the protein or salt thereof according to (1) above or the partial peptide or salt thereof according to (3) above;

(16) A compound or salt thereof which inhibits or activates the enzyme activity of the protein or salt thereof according to (1) above, obtained by using the screening method according to (14) above or the screening kit according to (15) above;

(17) A pharmaceutical comprising the compound or salt thereof according to (16) above, and;

(18) The pharmaceutical or the like according to (17) above, wherein the pharmaceutical is a pharmaceutical for prevention or treatment of cancer.

Moreover, the present invention also provides:

(19) DNA comprising DNA having a base sequence which is hybridizable under highly stringent conditions with the base sequence represented by SEQ ID NO: 2.or SEQ ID NO: 12;

(20) A recombinant vector comprising the DNA according to (19) above;

(21) A transformant transformed by the recombinant vector according to (20) above;

(22) A method for manufacturing the protein or salt thereof encoded by the DNA according to (19) above, wherein the transformant according to (21) above is cultured to produce the protein encoded by the DNA according to (19) above, which is then accumulated and collected;

(23) The protein or salt thereof encoded by the DNA according to (19) above, produced by the method according to (22) above;

(24) A method for quantifying the protein or salt thereof according to (1) above or the partial peptide or salt thereof according to (3) above in a test solution, wherein the antibody according to (12) above is reacted competitively with a test solution and the labeled protein according to (1) above or partial peptide according to (3) above or salts of these, and the proportion of the labeled protein or salt thereof according to (1) above or partial peptide or salt thereof according to (3) above, which binds to the antibody is measured.

(25) A method for quantifying the protein,or salt thereof according to (1) above or the partial peptide or salt thereof according to (3) above in a test solution, wherein the test solution is reacted either simultaneously or consecutively with an antibody according to (12) above which has been insolibilized on a carrier-and another, labeled antibody according to (12) above, and the activity of the labeling agent on the insolibilizing carrier is measured;

(26) A pharmaceutical comprising the antibody according to (12) above (preferably, an antibody which acts to neutralize the activity of the protein according to (1) above);

(27) The pharmaceutical according to (26) above which is a therapeutic agent for cancer;

(28) A method for screening a compound or salt thereof which inhibits or activates the enzyme activity (such as ribonucleotide reductase activity or the like) of the protein or salt thereof according to (1) above, wherein the enzyme activity of the protein or salt thereof according to (1) above or the partial peptide or salt thereof according to (3) above is measured and compared when (i) a substrate is brought into contact with the protein or salt thereof according to (1) above or the partial peptide or salt thereof according to (3) above, and when (ii) a substrate and a test compound are brought into contact with the protein or salt thereof according to (1) above or the partial peptide or salt thereof according to (3) above.

(29) An antisense oligonucleotide having a base sequence, which is complementary or substantially complementary to the DNA according to (1) or (19) above, and having an action that can control the expression of said DNA;

(30) The antisense oligonucleotide according to (29) above, wherein the base sequence which is substantially complementary to the DNA according to (1) or (19) above is a base sequence having about 90% or greater (preferably about 95% or greater) homology with all or part of a base sequence which is complementary to said DNA.

(31) A pharmaceutical comprising the antisense oligonucleotide according to (29) or (30) above; and.

(32) A pharmaceutical according to (31) above which is a therapeutic agent for cancer.

BRIEF SPECIFICATION OF THE DRAWINGS

FIGS. 1A–1C show the base sequence (SEQ ID NO:2) of DNA encoding for the protein of the present invention obtained in Example 2, and the amino acid sequence which is encoded by it (SEQ ID NO:1).

FIG. 2 shows a comparison of homologies on the amino acid sequences of the protein of the present invention obtained in Example 2 (upper; SEQ ID NO: 1) and ribonucleotide reductase (lower; SEQ ID NO: 5).

BEST MODE FOR CARRYING OUT THE INVENTION

Figure 3:
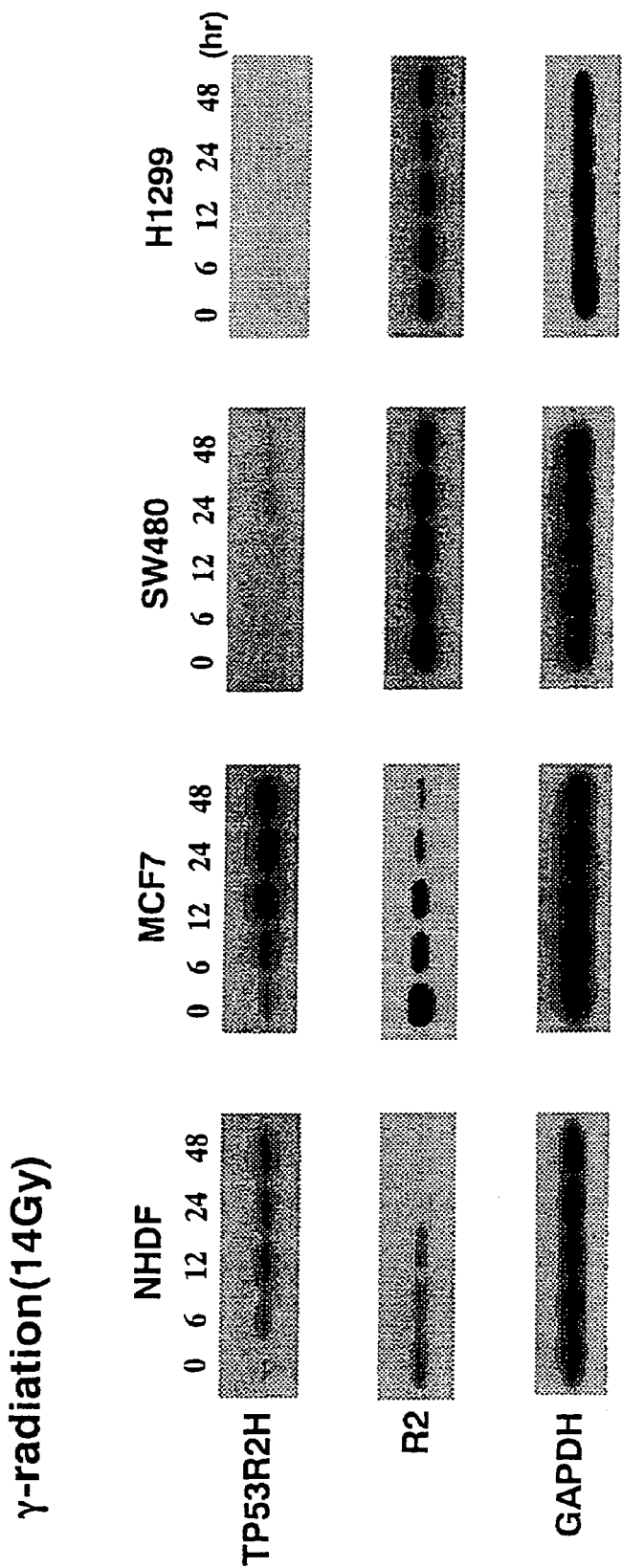
FIG. 3 shows changes in the expressed amounts of R2 mRNA and TP53R2H mRNA after DNA damage obtained in Example 3.

The protein of the present invention is a protein comprising the amino acid sequence represented by SEQ ID NO: 1 or a substantially identical amino acid sequence.

The protein of the present invention may be a synthetic protein or a protein derived from any cells (for example spleen cells, nerve cells, gliacytes, pancreatic β cells, bone marrow cells, mesangial cells, Langerhans' cells, epidermal cells, epithelial cells, endothelial cells, fibroblast cells, fiber cells, muscle cells, fat cells, immune cells (such as macrophages, T-cells, B-cells, natural killer cells, mast cells, neutrophils, basophils, eosinophils or monocytes), megakaryocytes, synovial cells, cartilage cells, bone cells, osteoblasts, osteoclasts, mammary gland cells, liver cells or interstitial cells, or precursor cells, stem cells or cancer cells of these cells) of warm blooded animals (for example humans, guinea pigs, rats, mice, chickens, rabbist, pigs, sheep, cows, monkeys or the like), or from tissue in which these cells are present, such as the brain, various parts of the brain (for example the olfactory bulb, amygdaloid nucleus, cerebral basal ganglia, hippocampus, thalamus, hypothalamus, cerebral cortex, medulla oblongata, cerebellum, occipital lobe, frontal lobe, temporal lobe, putamen, caudate nucleus, cerebral gland or substantia nigra), the spinal cord, pituitary gland, stomach, pancreas, kidneys, liver, gonads, thyroid gland, gall bladder, bone marrow, adrenal gland, skin, muscle, lungs, digestive tract (for example the large or small intestine). blood vessels, heart, thymus, spleen, submandibular gland, peripheral blood, prostate, testes, ovaries, placenta, uterus, bone, joints, skeletal muscle and the like.

An example of an amino acid sequence substantially identical to SEQ ID NO: 1 includes an amino acid sequence with homology of about 90% or more or preferably about 95% or more with the amino acid sequence represented by SEQ ID NO: 1.

A protein for example having an amino acid sequence substantially identical to said SEQ ID NO : 1 and having substantially the same activity as a protein comprising the amino acid sequence represented by SEQ ID NO: 1 can be used as the protein of the present invention comprising an amino acid sequence substantially identical to SEQ ID NO: 1.

"Substantially the same activity" refers for example to ribonucleotide reductase activity or other enzyme (preferably ribonucleotide reductase) activity involved in nucleic acid metabolism. "Substantially the same" indicates that the activities are the same in character (physiochemically or pharmacologically, for example). Thus for example the ribonucleotide reductase or other activity should be similar (for example about 0.01–100 times, or preferably about 0.5–20 times, or more preferably about 0.5–2 times), but there may be differences in the degree of such activity and in other quantitative elements such as the molecular weight of the protein.

Ribonucleotide reductase activity can be measured in accordance with a publicly known method. For example, it can be measured by the method described below for screening pharmaceutical candidate compounds.

In addition, a protein comprising (1) an amino acid sequence in which 1 or 2 or more (preferably about 1–30, more preferably about 1–20, still more preferably about 1–10, most preferably about 1–5) amino acids are deleted from the amino acid sequence represented by SEQ ID NO: 1, (2) an amino acid sequence in which 1 or 2 or more (preferably about 1–30, more preferably about 1–20, still more preferably about 1–10, or most preferably about 1–5) amino acids are added to the amino acid sequence represented by SEQ ID NO: 1, (3) an amino acid sequence in which 1 or 2 or more (preferably about 1–30, more preferably about 1–20, still more preferably about 1–10, or most preferably about 1–5) of the amino acids in the amino acid sequence represented by SEQ ID NO: 1 are substituted by other amino acids, or (4) a combination of such amino acids may be used as the protein of the present invention.

In accordance with conventional description of peptides, the left terminus of proteins in the present Specification is the N terminus (amino terminus) and the right terminus is the C terminus (carboxyl terminus). In the protein of the present invention including a protein comprising the amino acid sequence represented by SEQ ID NO: 1, the C-terminus is usually in the form of a carboxyl group (—COOH) or carboxylate (—COO⁻) for the C terminus, but may also be in the form of an amide (—CONH$_2$) or ester (—COOR).

A methyl, ethyl, n-propyl, isopropyl, n-butyl or other $C_{1-6}$ alkyl group for example, or a cyclopentyl, cyclohexyl or other $C_{3-8}$ cycloalkyl group for example, or a phenyl, α-naphthyl or other $C_{6-12}$ allyl group, for example, or a benzyl, phenethyl or other phenyl-$C_{1-2}$ alkyl group or α-naphthylmethyl or other α-napthyl-$C_{1-2}$ alkyl group or other $C_{7-14}$ aralkyl group or pivaloyloxymethyl group or the like can be used as the R in this ester.

The protein of the present invention includes proteins with amidified or esterified carboxyl groups in cases where the protein of the present invention has a carboxyl group (or carboxylate) somewhere other than the C terminus. In such cases, the C terminus ester described above among others can be used as the ester.

Moreover, the protein of the present invention also includes those in which the amino group of the N terminus amino acid residue (such as a methionine residue) is protected by a protective group (such as a formyl group, acetyl group or other $C_{1-6}$ alkanoyl or other $C_{1-6}$ acyl group or the like), those in which the N terminus end is severed in vivo and the resulting glutamyl group pyroglutamated, and those in which substituents (such as —OH, —SH and amino, imidazole, indole and guanidino groups and the like) on side chains of amino acids in the molecule are protected by suitable protective groups (such as formyl, acetyl and other $C_{1-6}$ alkanoyl and other $C_{1-6}$ acyl groups and the like), as well as conjugated proteins such as the so-called glycoproteins, which have bound sugar chains.

Specific examples of the protein of the present invention include for example the human derived protein having the amino acid sequence represented by SEQ ID NO: 1.

The partial peptide of the protein of the present invention may be any partial peptide of the protein of the present invention described above, but includes, for example a peptide having an amino acid sequence of at least 10 or more, preferably 50 or more, more preferably 100 or more of the constituent amino acids of the protein of the present invention, and preferably having ribonucleotide reductase activity or other enzyme activity involved in nucleic acid metabolism.

Moreover, a partial peptide comprising (1) an amino acid sequence in which 1 or 2 or more (such as 1–20, preferably about 1–10, more preferably a few (such as 1–5)) amino acids are deleted from the amino acid sequence represented by SEQ ID NO: 1, (2) an amino acid sequence in which 1 or 2 or more (such as 1–20, preferably about 1–10, or more preferably a few (such as 1–5)) amino acids are added to the amino acid sequence represented by SEQ ID NO: 7, SEQ ID NO: 8 or SEQ ID NO: 9, (3) an amino acid sequence in which 1 or 2 or more (such as 1–20, preferably about 1–10, or more preferably a few (such as 1–5)) of the amino acids in the amino acid sequence represented by SEQ ID NO: 7, SEQ ID NO: 8 or SEQ ID NO: 9 are substituted by other amino acids, or (4) a combination of such amino acids may be used as the partial peptide of the present invention.

Moreover, the partial peptide of the present invention ordinarily has a carboxyl group (—COOH) or carboxylate (—COO⁻) for the C terminus, but as in the case of the aforementioned protein of the present invention, the C terminus may also be in the form of an amide (—CONH$_2$) or ester (—COOR) (with R being defined as above).

In addition, as in the case of the aforementioned protein of the present invention, the partial peptide of the present invention also includes those in which the amino group of the N terminus amino acid residue (such as a methionine residue) is protected by a protective group, those in which the N terminus end is severed in vivo and the resulting glutamyl group pyroglutamated, and those in which substituents on side chains of amino acids in the molecule are protected by suitable protective groups, as well as conjugated proteins such as the so-called glycoproteins, which have bound sugar chains.

Since the partial peptide of the present invention can be used as an antigen for purposes of antibody production, it does not necessarily have to have ribonucleotide reductase activity or other enzyme (preferably ribonucleotide reductase) activity involved in nucleic acid metabolism.

Salts with physiologically acceptable acids (such as inorganic and organic acids) or bases (such as alkali metals) can be use as the salts of the protein or partial peptide of the present invention. The physiologically acceptable acid addition salts are particularly desirable. For example, salts with inorganic acids (such as hydrochloric acid, phosphoric acid, hydrobromic acid or sulphuric acid) or with organic acids (such as acetic acid, formic acid, propionic acid, fumaric acid, maleic acid, succinic acid, tartaric acid, citric acid, malic acid, oxalic acid, benzoic acid, methanesulfonic acid or benzenesulfonic acid) and the like may be used.

The protein or salt thereof or partial peptide or salt thereof of the present invention can be manufactured by publicly known methods for purifying proteins or peptides from the aforementioned cells or tissues of warm-blooded animals. It can also be manufactured by culturing the transformant mentioned below comprising DNA encoding the protein or partial peptide. Further, it can be manufactured by the peptide synthesis method mentioned below or by modifications thereof.

When the protein, partial peptide or salt thereof of the present invention is manufactured from the tissue or cells of a warm-blooded animal, the tissue or cells of the warm-blooded animal are first homogenized and then extracted with an acid or the like. The extract can be purified and isolated by a combination of methods including methods utilizing solubility, such as salting out or solvent precipitation; methods utilizing mainly differences in molecular weight, such as dialysis, ultrafiltration, gel filtration or SDS-polyacrylamide gel electrophoresis; methods utilizing differences in electric charge, such as ion exchange chromatography; methods utilizing specific affinity, such as affinity chromatography; methods utilizing differences in hydrophobicity, such as reversed phase high performance liquid chromatography; and methods utilizing isoelectric point differences, such as isoelectric focusing.

Ordinary commercial resins for protein synthesis can be used in synthesizing the protein or partial peptide or their salts of the present invention, or an amide of these. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetoamidomethyl resin, polyacrylamide resin, 4-(2',4'-dimethoxyphenyl-hydroxymethyl) phenoxy resin and 4-(2',4'-dimethoxyphenyl-Fmoc aminoethyl) phenoxy resin. Using such resins, amino acids in which α-amino and functional groups on the side chains are suitably protected are condensed on the resin according to various publicly known condensation methods, following the sequence of the target protein or partial peptide. At the end of the reaction, the protein or partial peptide is excised from the resin and the various protective groups are removed at the same time. An intramolecular disulfide bond-forming reaction is then performed in a highly dilute solution, and the objective protein, partial protein or amide of these is obtained.

Various activating reagents, which can be utilized in protein synthesis can be used in condensing the protected amino acids. Carbodiimides are particularly suitable. Carbodiimides include DCC, N,N'-diisopropylcarbodiimide and N-ethyl-N'-(3-dimethylaminoprolyl) carbodiimide. For purposes of activation, either the protected amino acids can be added directly to the resin together with a racemization inhibitor (such as HOBt, HOOBt or the like), or the protected amino acids can be first activated either as symmetrical acid anhydrides or HOBt or HOOBt esters, and then added to the resin.

The solvents used in activating the protected amino acids and condensing them with resin may be selected as needed from known solvents used in protein condensation reactions. For example, N,N-dimethylformamide, N,N-dimethylactamide, N-methylpyrolidone and other acid amides, methylene chloride, chloroform and other halogenated hydrocarbons, trifluoroethanol and other alcohols, dimethylsulfoxide and other sulfoxides, DMF, pyridine, dioxane, tetrahydrofuran and other ethers, acetonitrile, propionitrile and other nitrites, methyl acetate, ethyl acetate and other esters, as well as suitable mixtures of these can be used. A reaction temperature can be selected from the range known to be applicable for protein bond-forming reactions, and normally a temperature between about −20° C. and 50° C. is selected. The activated amino acid derivatives are generally used in an excess of 1.5–4 times. If results of tests using ninhydrine show insufficient condensation, condensation can be completed by repeating the condensation reaction without removal of the protective groups. If sufficient condensation is not achieved even by repetition of the reaction, unreacted amino acids can be acetylated with acetic anhydride or acetylimidazole to cancel any possible adverse effect of the subsequent reaction.

Protective groups for the starting amino groups include for example Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl and Fmoc.

Carboxyl groups can be protected for example by alkyl esterification (straight-chain, branching or cyclic alkylesterification of methyl, ethyl, propyl, butyl, t-butyl, cyclopentyl, cyclohexyl, cycloheptyl, cyclooctyl or 2-adamantyl, for example), aralkyl esterification (benzyl ester, 4-nitrobenzyl ester, 4-methoxybenzyl ester, 4-chlorobenzyl ester or benzhydryl esterification, for example), phenacyl esterification, benzyloxycarbonyl hydrazidification, t-butoxycarbonyl hydrazidification or trityl hydrazidification.

Serine hydroxyl groups can be protected for example by esterification or etherification. Groups that are suitable for esterification include for example acetyl groups and other lower alkanoyl groups, benzoyl groups and other aroyl groups, benzyloxycarbonyl groups and ethoxycarbonyl groups and other groups derived from carbonic acid. Groups that are suitable for etherification include for example benzyl groups, tetrahydropyranyl groups and t-butyl groups.

Bzl, $Cl_2$-Bzl, 2-nitrobenzyl, Br-Z and t-butyl groups for example can be used to protect the phenolic hydroxyl group of tyrosine.

Tos, 4-methoxy-2,3,6-trimethylbenzenesulfonyl, DNP, benzyloxymethyl, Bum, Boc, Trt and Fmoc groups for example can be used to protect the imidazole moiety of histidine.

Examples of activated carboxyl groups in the starting materials include the corresponding acid anhydrides, azides, activated esters (esters with alcohols such as pentachlorophenol, 2,4,5-trichlorophenol, 2,4-dinitrophenol, cyanomethyl alcohol, paranitrophenol, HONB, N-hydroxysuccimide, N-hydroxyphthalimide or HOBt) and the like. Corresponding phosphoric acid amides for example can be used as the activated amino groups in the starting material.

Methods of eliminating (splitting off) the protective groups include for example catalytic reduction in a hydrogen gas flow in the presence of a catalyst such as Pd-black or Pd-carbon, treatment with an acid such as an hydrous hydrogen fluoride, methanesulfonic acid, trifluoromethanesulfonic acid, trifluoroacetic acid or a mixture thereof or the like, treatment with a base such as diisopropylethylamine, triethylamine, piperidine, piperazine or the like, or reduction with sodium in liquid ammonia. Elimination by acid treatment as described above is general performed at a temperature of approximately −20° C. to 40° C., and addition of cationic scavengers such as anisole, phenol, thioanisole, metacresol, paracresol, dimethylsulfide, 1,4-butanedithiol and 1,2-ethanedithiol is effective in the acid treatment. Moreover, the 2,4-dinitrophenyl group used in protecting the imidazole group of histidine is removed by thiophenol treatment, while the formyl group which is used in protecting the indole group of tryptophan is removed by the aforesaid acid treatment in the presence of 1,2-ethanedithiol or 1,4-butanedithiol or the like, as well as by treatment with an alkali such as a dilute sodium hydroxide solution, dilute ammonia or the like.

Publicly known groups and means can be appropriately selected for protection of a functional group which should not participate in the reaction of the starting material and its protecting group as well as removal of the protecting group, activation of a functional group which participates in the reaction, and the like.

In another method for obtaining an amide of the protein or partial peptide of the present invention, the α-carboxyl group of the carboxy terminal amino acid is first amidated, the peptide chain (protein chain) is extended toward the amino group side to the desired chain length, and then only the protective group of the N-terminal α-amino group of the peptide chain is removed to obtain a protein. Another protein is produced by removing only the protective group of the C-terminal carboxyl group, and the two proteins are condensed together in a solvent mixture as described above. The details of the condensation reaction are as described above. The protected protein obtained by condensation is first purified, and then all protective groups can be removed by the aforementioned methods to obtain the desired crude protein. This crude protein can then be purified by various well-known purification methods, and the main fraction is lyophilized to obtain an amide of the desired protein or partial peptide thereof.

To obtain an ester of the protein or partial peptide thereof of the present invention, the α-carboxyl group of the carboxy terminal amino acid is first condensed with a desired alcohol to produce an amino acid ester, and the desired ester of the protein or partial peptide thereof can then be obtained in the same way as the amide of the protein or partial peptide thereof.

The partial peptide or salt thereof of the present invention can be manufactured either according to publicly known methods of peptide synthesis, or by cutting the protein of the present invention with a suitable peptidase.

Possible methods of peptide synthesis include for example either solid phase synthesis or liquid phase synthesis. In other words, the partial peptides or amino acids which are to form the target peptide are condensed with the rests, and if the product has protective groups the protective groups are removed to produce the target peptide. Publicly known methods for condensation and protective group removal include for example the methods described in (1) through (5) below.

(1) Bodanszky, M. & M. A. Ondetti, *Peptide Synthesis*, Interscience Publishers, New York (1966)

(2) Schroeder & Luebke, *The Peptide*, Academic Press, New York (1965)

(3) Izumiya, Nobuo et al, *Fundamental and Experimental Peptide Synthesis*, Maruzen (1975)

(4) Yajima, Haruaki and Shunpei Sakakibara, *A Course of Biochemical Experiments* 1, *Protein Chemistry IV*, 205 (1977)

(5) Yajima, Haruaki Ed., *Drug Development Continued*, Vol. 14, *Peptide Synthesis*, Hirokawa Shoten Following the reaction, the target peptide can be purified and isolated by a combination of ordinary methods, such as solvent extraction, distillation, column chromatography, liquid chromatography or recrystallization. When the peptide obtained by these methods is in a free form, it can be converted into a suitable salt by publicly known methods or modifications thereof. On the other hand, when the peptide is in the form of a salt, it can be converted into a free form or a different salt form by public known methods or modifications thereof.

The DNA encoding the protein of the present invention can be any DNA which comprises abase sequence encoding the said protein of the present invention. The DNA may be any one of genomic DNA, a genomic DNA library, cDNA derived from the cells or tissues described above, a cDNA library derived from the cells or tissues described above or synthetic DNA. The vector used for the library may be any one of bacteriophage, plasmid, cosmid, phagemid or the like. In addition, the DNA can be directly amplified by reverse transcriptase polymerase chain reaction (hereinafter abbreviated as RT-PCR technology) using total RNA or mRNA fraction purified from the cells or tissues described above.

Specifically, the DNA encoding the protein of the present invention having the amino acid sequence represented by SEQ ID NO: 1 may be (1) DNA having the base sequence represented by SEQ ID NO: 2, (2) DNA having the base sequence represented by SEQ ID NO: 12, (3) DNA comprising a base sequence which is hybridizable under highly stringent conditions with the base sequence represented by SEQ ID NO: 2 or SEQ ID NO: 12.

For example, DNA comprising a base sequence having about 90% or greater, or preferably about 95% or greater homology with the base sequence represented by SEQ ID NO: 2 or SEQ ID NO: 12 can be used as DNA which is hybridizable under highly stringent conditions with the base sequence represented by SEQ ID NO: 2 or SEQ ID NO: 12.

Hybridization can be accomplished by publicly known methods or modifications thereof, such as the methods described in Molecular Cloning $2^{nd}$ (J. Sambrook et al, Cold Spring Harbor Lab Press, 1989). When using a commercial cDNA library, mRNA library or kit, the methods described in the attached manuals can be employed. More preferablly, hybridization can be performed in accordance wih highly stringent conditions.

"Highly stringent conditions" indicates conditions of sodium concentration about 19–40 mM, or-preferably about 19–20 mM, and temperature about 50–70° C., or preferably about 60–65° C. A sodium concentration of about 19 mM and temperature of about 65° C. are particular desirable.

For example, DNA comprising DNA having the base sequence represented by SEQ ID NO: 2, SEQ ID NO: 3, SEQ ID NO: 4 or SEQ ID NO: 12 or the like (preferably DNA comprising DNA having the base sequence represented by SEQ ID NO: 2 or SEQ ID NO: 12) may be used as the DNA encoding the protein comprising the amino acid sequence represented by SEQ ID NO: 1.

The DNA encoding the partial peptide of the present invention may be any DNA which comprises a base sequence encoding the aforementioned partial peptide of the present invention. The DNA may be any one of genomic DNA, a genomic DNA library, cDNA derived from the cells or tissues described above, a cDNA library derived from the cells or tissues described above or synthetic DNA. The vector used for the library may be any one of bacteriophage, plasmid, cosmid, phagemid or the like. In addition, the DNA can be directly amplified by RT-PCR using a total RNA or mRNA fraction prepared from the cells or tissues described above.

Means for cloning the DNA encoding the protein or partial peptide of the present invention (sometimes abbreviated hereinafter as "the protein of the present invention") include (1) using a synthetic DNA primer having a partial base sequence of the DNA encoding the protein of the present invention, amplification of the target DNA from the aforementioned DNA library or the like by PCR, (2) selection by hybridization of DNA inserted into a suitable vector with a labeled DNA fragment encoding some or all regions of the protein of the present invention, or labeled synthetic DNA (probe). Hybridization can be performed for example according to the method described in *Molecular Cloning 2nd* (J. Sambrook et al, Cold Spring Harbor Lab Press, 1989). When using a commercial library or kit, the methods described in the attached manuals may be employed. The DNA encoding the partial peptide of the present invention can also be manufactured by publicly known methods of oligonucleotide synthesis.

Changes to the base sequence of DNA (deletion, addition, substitution) can be accomplished by publicly known methods such as the Gapped duplex or Kunkel method or similar methods, using well-known kits such as the Mutan™-G (Takara Shuzo Inc.) or Mutan™-K (Takara Shuzo Inc.).

The cloned DNA encoding the protein of the present invention can be used as it is, depending upon purpose or, if desired, after digestion with restriction enzymes or after addition of a linker thereto. The DNA may contain ATG as a translation initiation codon at the 5' end thereof and TAA, TGA or TAG as a translation termination codon at the 3' end thereof. These translation initiation and termination codons may also be added to the DNA, using an appropriate synthetic DNA adapter.

The expression vector for the DNA encoding the protein of the present invention can be manufactured, for example, by (a) excising the objective DNA fragment from the DNA encoding the protein of the present invention and then (b) ligating the DNA fragment downstream from a promoter in the appropriate expression vector.

Examples of the vector include plasmids derived form *E. coli* (for example pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ-phage and the like, animal viruses such as retrovirus, vaccinia virus, baculovirus and the like, and pA1-11, pXT1, pRc/CMV, pRc/RSV, pcDNAI/Neo and the like.

The promoter used in the present invention may be any promoter so long as it matches well with the host to be used for gene expression. When animal cells are used as the host for example, possible promoters include SRα promoter, SV40 promoter, LTR promoter, CMV (cytomegalovirus) promoter, HSV-TK promoter and the like. Among them, CMV promoter and SRα promoter are used preferably. Where the host is bacteria of the genus *Escherichia*, preferred examples include trp promoter, lac promoter, recA promoter, λ$P_L$ promoter, lpp promoter, T7 promoter and the like. When bacteria of the genus *Bacillus* are used as the host, preferred examples are SPO1 promoter, SPO2 promoter, penP promoter and the like. When yeast is used as the host, preferred examples are PHO5 promoter, PGK promoter, GAP promoter, ADH promoter, AOX1 promoter and the like. When insect cells are used as the host, preferred examples include polyhedrin promoter, P10 promoter and the like.

In addition to the aforesaid examples, an expression vector may be used that contains an optional enhancer, splicing signal, polyA addition signal, selection marker, SV40 replication origin (hereinafter sometimes abbreviated as SV40ori) or the like. Examples of the selection marker include dihydrofolate reductase (hereinafter sometimes abbreviated as dhfr) gene [methotrexate (MTX) resistant], ampicillin resistant gene (hereinafter sometimes abbreviated as Amp$^r$), neomycin resistant gene (hereinafter sometimes abbreviated as Neo; G418 resistant) and the like. In particular, when the dhfr gene is used as the selection marker using dhfr gene deficient Chinese hamster cell CHO, selection of cells transformed by the target gene may also be effected in a thymidine-free medium.

If necessary and desired, a signal sequence that matches the host is added to the N-terminal side of the protein. Examples of signal sequences that can be utilized include alkaliphosphatase signal sequence, OmpA signal sequence and the like when the host is bacteria of the genus *Escherichia*; α-amylase signal sequence, subtilis in signal sequence and the like when the host is bacteria of the genus *Bacillus*; MFα signal sequence, SUC2 signal sequence and the like when the host is yeast; and insulin signal sequence, α-interferon signal sequence, antibody molecule signal sequence and the like when the host is animal cells, respectively.

Transformants can be manufactured by introducing into cells a vector containing DNA constructed in this way that encodes the protein of the present invention.

As the host, there may be employed, for example, bacteria belonging to the genus *Escherichia*, bacteria belonging to the genus *Bacillus*, yeast, insects or insect cells, animal cells, etc.

Examples of bacteria belonging to the genus *Escherichia* that can be used include *Escherichia coli* K12 DH1 (*Proc. Natl. Acad. Sci. U.S.A.*, Vol. 60, 160 (1968)), JM103 (*Nucleic Acids Research*, Vol. 9, 309 (1981)), JA221 (*Journal of Molecular Biology*, Vol.120, 517 (1978)), HB101 (*Journal of Molecular Biology*, Vol. 41, 459 (1969)), C600 (*Genetics*, Vol. 39, 440 (1954)) and the like.

Examples of bacteria belonging to the genus *Bacillus* that can be used include *Bacillus subtilis* MI114 (*Gene*, Vol. 24, 255 (1983)), 207–21 (*Journal of Biochemistry*, Vol. 95, 87 (1984)) and the like.

Yeasts such as for example *Saccharomyces cerevisiae* AH22, AH22R-, NA87-11A, DKD-5D, 20B-12, *Schizosaccharomyces pombe* NCYC1913, NCYC2036 and *Pichia pastoris* KM71 can be used.

Examples of insect cells that can be used include *Spodoptera frugiperda* cells (Sf cells), MG1 cells derived from the mid-intestine of *Trichoplusia ni*, High Five™ cells derived from eggs of *Trichoplusia ni*, cells derived from *Mamestra brassicae*, cells derived from *Estigmena acrea*, etc. for AcNPV virus; and for BmNPV virus, *Bombyx mori* N cells (BmN cell), etc. Examples of Sf cells that can be used include Sf9 cells (ATCC CRL1711), Sf21 cells [both cells are described in Vaughn, J. L. et al., In Vivo, Vol. 13, 213–217 (1977)], etc.

Insects that can be used include for example *Bombyx mori* larvae (Maeda et al, *Nature*, Vol. 315, 592 (1985)).

Animal cells that can be used include for example monkey COS-7 cells, Vero cells, Chinese hamster CHO cells (abbreviated hereinafter as "CHO cells", dhfr gene deficient Chinese hamster CHO cells (abbreviated hereinafter as CHO (dhfr⁻) cells), mouse L cells, mouse AtT-20 cells, mouse myeloma cells, rat GH3 cells, human FL cells, 293 cells, C127 cells, BALB/3T3 cells, Sp-2 cells and the like. CHO cells, CHO (dhfr⁻) cells, 293 cells and the like are preferred.

Bacteria belonging to the genus *Escherichia* can be transformed, for example, by the method described in *Proc. Natl. Acad. Sci. U.S.A.*, Vol. 69, 2110 (1972) or *Gene*, Vol. 17, 107 (1982), etc.

Bacteria belonging to the genus *Bacillus* can be transformed, for example, by the method described in *Molecular & General Genetics*, Vol. 168, 111 (1979), etc.

Yeast can be transformed, for example, by the method described in *Methods in Enzymology*, Vol. 194, 182–187 (1991), or by the method described in *Proc. Natl. Acad. Sci. U.S.A.*, Vol. 75, 1929 (1978).

Insect cells or insects can be transformed, for example, according to the method described in *Bio/Technology*, Vol. 6, 47–55(1988), etc.

Animal cells can be transformed, for example, according to the method described in *Saibokogaku Bessatsu* 8, *Shin Saibokogaku Jikken Protocol*, 263–267 (1995) (shujunsha), or the method described in *Virology*, Vol. 52, 456 (1973).

Methods for introducing the expression vectors into the cells include, for example, the calcium phosphate method (Graham, F. L. and van der Eb, A. J., *Virology* 52, 456–467 (1973)), the electroporation method (Nuemann, E. et al., *EMBO Journal* 1, 841–845 (1982)), etc.

Transformants transformed with expression vectors comprising DNA encoding the protein of the present invention can be obtained as described above.

One method for stably expressing the protein of the present invention with animal cells is to select by clone selection the cells in which the expression vectors transfected to animal cells are introduced into chromosomes. Specifically, the transformants are selected using as an index the selection marker described above. By then repeating clone selection on the animal cells thus obtained using the selection marker, it is possible to obtain a stable animal cell line capable of highly expressing the protein of the present invention. When the dhfr gene is used as the selection marker, cultivation can be performed by gradually increasing the level of MTX to select resistant cells so that the DNA encoding the protein of the present invention can be amplified in the cells together with the dhfr gene to obtain an animal cell line with still higher expression.

The protein or salt thereof of the present invention can be manufactured by cultivating the transformant described above under conditions in which the DNA encoding the protein of the present invention can be expressed, to produce and accumulate the protein of the present invention.

Where the host is a bacterium belonging to the genus *Escherichia* or the genus *Bacillus*, the transformant can be appropriately cultivated in a liquid medium which contains materials required for growth of the transformant, such as carbon sources, nitrogen sources, inorganic materials, etc. Examples of carbon sources include glucose, dextrin, soluble starch, sucrose, etc. Examples of nitrogen sources include inorganic or organic materials such as ammonium salts, nitrates, corn steep liquor, peptone, casein, meat extract, soybean cake, potato extract, etc. Examples of inorganic materials are calcium chloride, sodium dihydrogenphosphate, magnesium chloride, etc. In addition, yeast extract, vitamins, growth promoting factors, etc. may also be added to the medium. Preferably, the pH of the medium is adjusted to about 5 to 8.

A preferred example of a medium for cultivation of bacteria belonging to the genus *Escherichia* is M9 medium supplemented with glucose and casamino acids (Miller, *Journal of Experiments in Molecular Genetics* 431–433, Cold Spring Harbor Laboratory, New York, 1972). If necessary and desired, a chemical such as 3β-indolylacrylic acid can be added to the medium in order to improve the efficiency of the promoter.

Where the host is a bacterium belonging to the genus *Escherichia*, the transformant is usually cultivated at about 15 to 43° C. for about 3 to 24 hours. If necessary and desired, the culture may be aerated or agitated.

Where the host is a bacterium belonging to the genus *Bacillus*, the transformant is usually cultivated at about 30° C. to 40° C. for about 6 to 24 hours. If necessary and desired, the culture can be aerated or agitated.

Media which can be used for cultivating a transformant whose host is a yeast include Burkholder's minimal medium (Bostian, K. L. et al., *Proc. Natl. Acad. Sci. U.S.A.*, Vol. 77, 4505 (1980)) or SD medium containing 0.5% casamino acids (Bitter, G. A. et al., *Proc. Natl. Acad. Sci. U.S.A.*, Vol. 81, 5330 (1984)). Preferably, the pH of the medium is adjusted to about 5 to 8. In general, the transformant is cultivated at about 20° C. to 35° C. for about 24 to 72 hours. If necessary and desired, the culture can be aerated or agitated.

Media which can be used for cultivating a transformant whose host is an insect cell or insect include Grace's Insect Medium (Grace, T. C. C., *Nature* 195, 788 (1962)) supplemented with 10% inactivated bovine serum or the like as appropriate. Preferably, the pH of the medium is adjusted to about 6.2 to 6.4. Normally, the transformant is cultivated at about 27° C. for about 3 to 5 days, and the culture can be aerated or agitated if necessary.

Media which can be used for cultivating a transformant whose host is an animal cell include MEM medium containing about 5% to 20% fetal bovine serum (*Science*, Vol. 122, 501 (1952)), DMEM medium [*Virology*, Vol. 8, 396 (1959)], RPMI 1640 medium (*J. Amer. Med. Ass.*, Vol. 199, 519 (1967)), 199 medium (*Proc. Soc. Biol. Med.*, Vol. 73, 1 (1950)) and the like The pH should be about 6–8. The transformant is usually cultivated at about 30° C. to 40° C. for about 15 hours to 72 hours, and the culture can be aerated or agitated if necessary.

Especially when CHO (dhfr⁻) cells and the dhfr gene are employed as the selection markers, it is preferable to use substantially thymidine-free DMEM supplemented with dialyzed bovine fetal serum.

In this way, a transformant can be made to produce the protein of the present invention.

The protein of the present invention can be separated and purified from the culture described above by the following procedures.

In one method for extracting the protein of the present invention from cultured bacteria or cells, the bacteria or cells can be collected after cultivation by publicly known methods, suspended in an appropriate buffer and disrupted by ultrasonication, lysozyme treatment and/or freeze-thaw cycling, after which a crude extract of the protein of the present invention is obtained by centrifugation, filtration, etc. The buffer may contain a protein denaturant such as urea or guanidine hydrochloride, or a surfactant such as Triton X-100™ or the like.

When the protein is secreted in the culture broth, the supernatant can be separated from the bacteria or cell after cultivation by publicly known method, and the supernatant is collected. The protein of the present invention, which is contained in the thus-obtained culture supernatant or extract, can be purified by a suitable combination of publicly known methods of separation and purification. Such known methods of separation and purification include methods utilizing solubility, such as salting out or solvent precipitation; methods utilizing mainly differences in molecular weight, such as dialysis, ultrafiltration, gel filtration or SDS-polyacrylamide gel electrophoresis; methods utilizing differences in electric charge, such as ion exchange chromatography; methods utilizing specific affinity, such as affinity chromatography; methods utilizing differences in hydrophobicity, such as reversed phase high performance liquid chromatography; and methods utilizing isoelectric point differences, such as isoelectric focusing.

When the protein of the present invention thus obtained is in a free form, it can be converted into a salt by publicly known methods or modifications thereof. On the other hand, when the protein is obtained in a salt form, it can be converted into a free form or a different salt form by publicly known methods or modifications thereof.

The protein of the present invention, which is produced by the recombinant, can be optionally modified or polypeptides partially deleted therefrom by treatment with an appropriate protein modifying enzyme prior to or after purification. Examples of protein modifying enzymes which can be used include trypsin, chymotrypsin, arginyl endopeptidase, protein kinase, glycosidase and the like.

The existence or activity of the thus formed protein of the present invention can be detected or assayed by enzyme immunoassay using a specific antibody, or the like.

The antibody to the protein or partial peptide thereof or salts of these of the present invention (sometimes abbreviated hereinafter as the protein, etc. of the present invention) maybe either a polyclonal or a monoclonal antibody, as long as it is capable of recognizing the protein or partial peptide thereof or salts of these of the present invention. Moreover, the antibody to the protein, etc. of the present invention may also have the ability to neutralize the activity of the protein, etc. of the present invention.

The antibody to the protein, etc. of the present invention can be manufactured according to publicly known methods of manufacturing antibodies or antiserums, using the protein, etc. of the present invention as an antigen.

[Preparation of Monoclonal Antibodies]

(a) Preparation of Monoclonal Antibody-Producing Cells

The protein, etc. of the present invention is administered either by itself or together with a carrier or diluent to a warm-blooded animal at a site where administration can result in antibody production. Complete Freund's adjuvant or incomplete Freund's adjuvant may also be administered at the same time in order to enhance antibody production capability. Administration is normally performed once every 2–6 weeks for a total of 2–10 administrations. Warm-blooded animals which may be used include monkeys, rabbits, dogs, guinea pigs, mice, rats, sheep, goats and chickens, and mice and rats are used preferably.

When preparing monoclonal antibody-producing cells, from warm-blooded animals that have been immunized with the antigen, for example, mice, indivisuals recognizing for antibody titer are selected and the spleens and lymph nodes are removed 2–5 days after the final immunization. The antibody-producing cells therein can then be fused with myeloma cells to prepare a monoclonal antibody-producing hybridoma. Antibody titer in antiserum can be measured for example by first reacting the labeled protein, etc. described below with the antiserum, and then measuring the activity of the labeling agent bound to the antibodies. Fusion can be accomplished by well-known methods, such that of Kohler and Millstein (*Nature,* Vol. 256, 495 (1975)). Fusion accelerators that can be used include polyethylene glycol (PEG) and Sendai virus, for example. PEG is used preferably.

Myeloma cells include for example myeloma cells of warm-blooded animals such as NS-1, P3U1, SP2/0, and AP-1, and P3U1 is used preferably. A preferable ratio of number of antibody-producing cells (spleen cells) and myeloma cells used is between about 1:1 and 20:1. PEG (preferably PEG1000-PEG6000) is added at a concentration of about 10–80%, and efficient cell fusion is achieved through incubation for 1–10 minutes at a temperature of about 20–40° C. or preferably about 30–37° C.

Various methods can be used to screen the monoclonal antibody-producing hybridoma, such as for example adding hybridoma culture supernatant to a solid phase (a microplate, for example) on which the antigen such as the protein has been adsorbed either directly or together with a carrier, then adding protein A or anti-immunoglobulin antibodies (such as mouse anti-immunoglobulin antibodies if mouse cells were used for cell fusion) labeled with a radioactive substance, enzyme or the like to detect the monoclonal antibodies bound to the solid phase; or adding hybridoma culture supernatant to a solid phase on which protein A or anti-immunoglobulin antibodies have been adsorbed, then adding the protein, etc. labeled with a radioactive substance, enzyme or the like to detect the monoclonal antibodies bound to the solid phase.

Selection of monoclonal antibodies can be accomplished by publicly known methods or modifications thereof, and is normally performed in animal cell medium to which HAT (hypoxanthine, aminopterin, thymidine) has been added. The medium used for selection and breeding can be any-medium in which the hybridoma can grow. Examples include RPMI 1640 medium containing 1–20% or preferably 10–20% fetal bovine serum, GIT medium (Wako Pure Chemical Industries, Ltd.) containing 1–10% fetal bovine serum, or hybridoma culture serum-free medium (SFM-101, Nissui Pharmaceutical Co., Ltd.). The culture temperature is 20–40° C. or preferably about 37° C. The culture time is normally 5 days to 3 weeks, or preferably 1 to 2 weeks. Culture can normally be performed in 5% carbon dioxide. The antibody titer of the hybridoma supernatant can be measured in the same way as the antibody titer of the antiserum described above.

(b) Purification of Monoclonal Antibodies

Separation and purification of monoclonal antibodies is similarly accomplished by the ordinary immunoglobulin separation and purification methods used for polyclonal antibodies (such as salting out, alcohol sedimentation, isoelectric point sedimentation, electrophoresis, adsorption-depsorption with anion exchanger (such as DEAE), ultra-centrifugation, gel filtration, or specific purification methods such as collection of the antibody alone with an active adsorbent such as an antigen bound solid phase, protein A or protein G, after which the bonds are released to obtain the antibodies).

[Preparation of Polyclonal Antibodies]

The polyclonal antibodies of the present invention can be manufactured by publicly known methods or modifications thereof. For example, a complex of an immune antigen (antigen such as the protein etc.) and a carrier protein is produced, warm-blooded animals are immunized by the same methods used above to produce monoclonal antibodies, substance containing antibodies to the protein, etc. of the present invention is collected from the immunized animals, and the antibodies are separated and purified.

In the complex of immune antigen and carrier protein used to immunize the warm-blooded animals, the type of carrier protein and the ratio of carrier to hapten may be selected at will and the proportion of bridging is not restricted as long as antibody production is efficient in response to the hapten when coupled with the carrier, but for example bovine serum albumin, bovine thyroglobulin, hemocyanin or the like can be coupled at a weight ratio of about 0.1–20 or preferably about 1–5 parts per 1 part of hapten.

A variety of condensing agents can be used for coupling the hapten and carrier, such as for example active ester reagents containing glutaraldehyde, carbodimmide, maleimide active ester, thiol groups or dithiopyridyl groups.

The condensation product is administered either by itself or together with a carrier or diluent to a warm-blooded animal at a site where antibodies can be produced. Complete Freund's adjuvant or incomplete Freund's adjuvant may also be administered at the same time in order to enhance antibody production capability. Administration is normally performed about once every 2–6 weeks for a total of about 3–10 administrations.

Polyclonal antibodies can then be collected from the blood or ascites, preferably from the blood of warm-blooded animals thus immunized.

Polyclonal antibody titer in antiserum can be measured by the same methods used above to measure antibody titer in hybridoma culture supernatant. The polyclonal antibodies can be separated and purified by the same methods for immunoglobulin used above to separate and purify monoclonal antibodies.

The antisense oligonucleotide having a base sequence which is complementary or substantially complementary to DNA or mRNA comprising a base sequence encoding the protein or partial peptide of the present invention (abbreviated hereinafter as "the DNA or mRNA of the present invention") may be any antisense oligonucleotide which is an oligonucleotide or derivative of an oligonucleotide having a base sequence which is complementary or substantially complementary to the DNA or mRNA of the present invention, and which is capable of suppressing expression of the protein, etc. of the present invention. Possibilities include antisense DNA and antisense RNA, particularly antisense DNA is preferred.

A base sequence which is substantially complementary to the DNA or mRNA of the present invention might be for example a base sequence having about 90% or greater or preferably about 95% or greater homology with all or part of a base sequence which is complementary to the DNA or mRNA of the present invention (that is, a complement strand of the DNA of the present invention). In particular, of the entire base sequence of the complement strand of the DNA or mRNA of the present invention, an antisense oligonucleotide is preferred which has about 90% or greater or preferably about 95% or greater homology with a complement strand of a part of the base sequence (such as a sequence near the initial codon) which encodes the N-terminal site of the protein, etc. of the present invention.

The antisense oligonucleotide normally consists of about 10–40 or preferably about 15–30 bases. In order to prevent degradation by nuclease or other hydrolytic enzymes, all or some of the phosphate residues of the nucleotides that make up the antisense oligonucleotide may be substituted with chemically modified phosphates, such as for example phosphorothioate, methylphosphonate or phosphorodithioate. Such antisense oligonucleotides can be manufactured by publicly known methods such as with a DNA synthesizer, for example.

The protein of the present invention has homology in its amino acid sequence with enzymes involved in nucleic acid metabolism, such as ribonucleotide reductase, for example. Consequently, the protein or partial peptide thereof or salt of these of the present invention may have ribonucleotide reductase or other enzyme activity related to nucleic acid metabolism. Therefore, it can be expected to (1) reduce the amount of ribonucleotide reductase or other enzymes in the body or (2) control the DNA synthesis pathway by inhibiting ribonucleotide reductase or other enzyme activity, thus enhancing the effects of anti-cancer agents and radiation therapy. Furthermore, because expression of the TP53R2H obtained in Example 2 below is induced during anti-cancer agent and radiation therapy, it may be involved even more than R2 in DNA repair. Consequently, effective therapeutic results might be achieved by suppressing the expression and activity of TP53R2H. Further, it is likely that if there are abnormalities of TP53R2H in normal cells, an inadequate supply of deoxyribonucleotide will mean that DNA repair does not proceed normally following DNA damage, leading to reduced DNA stability and susceptibility to cancer, so TP53R2 should also be useful in diagnosis.

Applications for the protein or salt thereof or partial peptide or salt thereof of the present invention (abbreviated hereinafter as "the protein, etc. of the present invention"), DNA encoding the protein, etc. of the present invention (abbreviated hereinafter as "the DNA of the present invention), antibodies to the protein, etc. of the present invention (abbreviated hereinafter as "the antibodies of the present invention") and antisense oligonucleotides are explained below.

(1) Drugs

The protein, etc. of the present invention or the DNA of the present invention are useful as pharmaceuticals such as pharmaceuticals for the prevention, etc. of defects in genes encoding for ribonucleotide reductase and other enzymes involved in nucleic acid metabolism and diseases caused by such defects as well as of depression of such enzyme activity and diseases caused by such depression (such as oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and other cancers).

For example, for patients in whom the activity of ribonucleotide reductase or other enzymes involved in nucleic acid metabolism is not adequately or normally expressed in the body because such enzymes are reduced or defective, the protein, etc. of the present invention can be restored to adequate or normal function by such means as (a) administering the DNA of the present invention to the patient so that the protein, etc. of the present invention is expressed in the body, (b) inserting the DNA of the present invention into cells so that the protein, etc. of the present invention is expressed, then transplanting said cells to the patient, (c) administering the protein, etc. of the present invention to the patient.

When the protein, etc. of the present invention is used as the aforementioned pharmaceutical, it is formulated either as a tablet, sugar-coated tablet, capsule, elixir or microcapsules, for example, and administered orally, or else as an injection such as a suspension or sterile solution together with water or another pharmaceutically acceptable liquid, and administered parenterally. For example, the protein, etc. of the present invention can be mixed with physiologically acceptable carriers, flavoring agents, excipients, vehicles, preservatives, stabilizers, binders and the like in a unit dosage form required for generally accepted pharmaceutical practice to prepare pharmaceutical preparations. The amount of active ingredients in these preparations is adjusted as to obtain appropriate doses within specified ranges. When the DNA of the present invention is used, it can be prepared by ordinary methods either alone or inserted into an appropriate vector such as a retrovirus vector, adenovirus vector or adenovirus-associated virus vector. The DNA of the present invention can be formulated either by itself or together with an adjuvant or other physiologically acceptable carrier for purposes of easy ingestion, and administered with a gene gun or hydrogel catheter or other catheter.

When the protein, etc. of the present invention is us d in said pharmaceutical form, protein, etc. which has been purified to at least 90%, preferably 95% or more, more preferably 98% or more, or most preferably 99% or more should be used.

Additives miscible with tablets, capsules, etc. include binders such as gelatin, corn starch, tragacanth and gum arabic, excipients such as crystalline cellulose, swelling agents such as corn starch, gelatin and alginic acid, lubricants such as magnesium stearate, sweeteners such as sucrose, lactose and saccharin, and flavoring agents such as peppermint, akamono oil and cherry. When the unit dosage is in the form of a capsule, liquid carriers such as oils and fats may further be used together with the additives described above. A sterile composition for injection may be formulated in a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of aqueous media for injection include physiological saline and isotonic solutions containing glucose and other auxiliary agents (e.g., D-sorbitol, D-mannitol, sodium chloride and the like), which may be used in combination with an appropriate dissolution aid such as an alcohol.(e.g., ethanol), a polyalcohol (e.g., propylene glycol or polyethylene glycol),.a nonionic surfactant (e.g., polysorbate 80™ or HCO-50), etc. Examples of oily media include sesame oil and soybean oil, which may also be used in combination with a dissolution aid such as benzyl benzoate or benzyl alcohol.

If necessary the formulation may also include a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant or the like. The pharmaceutical composition such as liquid for injection thus prepared is normally filled in an appropriate ampoule.

Vectors in which the DNA of the present invention is inserted are also prepared as above, and are normally administered parenterally.

Since the pharmaceutical preparation thus obtained is safe and of low toxicity, it can be administered safely to mammals (such as humans, rats, mice, guinea pigs, rabbits, sheep, pigs, cows, horses, cats, dogs, monkeys and the like).

The dose of the protein, etc. of the present invention varies depending on the target disease, the subject and the route of administration, etc., but when the protein, etc. of the present invention is administered orally for prevention of cancer, for example, the dose is normally about 0.1–100 mg, or preferably about 1.0–50 mg, or more preferably about 1.0–20 mg per day for adults (as 60 kg body weight). In parenteral administration, the single dose of the protein, etc. varies depending on the subject, the target disease and so forth, but for example when the protein, etc. of the present invention is administered for prevention of cancer in the form of an injection, it is advantageous to administer, for example, a daily dose of about 0.01–30 mg, preferably about 0.1–20 mg, or more preferably about 0.1–10 mg for adults (as 60 kg body weight). For other animal species, the corresponding dose as converted per 60 kg weight can be administered.

The DNA of the present invention can also be used as described above.

(2) Gene Diagnosis Agents

Since the DNA of the present invention can be used as a probe to detect abnormalities (genetic abnormalities) in DNA or mRNA encoding the protein, etc. of the present invention (abbreviated hereinafter as "the DNA or mRNA of the present invention") in mammals (such as humans, rats, mice, guinea pigs, rabbits, sheep, pigs, cows, horses, cats, dogs, monkeys, etc.), it can be used for example as a gene diagnosis agent to detect damage, defects, mutations or decreased expression of the DNA or mRNA of the present invention, as well as an increase in or excess expression of such DNA or mRNA and so forth.

Such gene diagnosis using the DNA of the present invention can be performed for example according to the publicly known northern hybridization and PCR-SSCP methods (*Genomics,* Vol. 5, 874–879(1989), *Proc. Natl. Acad. Sci. USA,* Vol. 86, 2766–2770 (1989)) and the like.

For example, when decreased expression of such mRNA is detected by northern hybridization, the diagnosis might be a disease such as cancer, or a high probability of contracting such a disease in the future.

On the other hand, if a cancer patient is found by northern hybridization to have excess expression of such mRNA, the diagnosis might be a high probability of cancer which is resistant to anti-cancer agents or radiation therapy.

If a mutation in the DNA is detected by the PCR-SSCP method, for example, the diagnosis might be a disease such as cancer, or a high probability of contracting such a disease in the future.

(3) Quantification of the Protein or Partial Peptide or their Salts of the Present Invention Since antibodies to the protein or partial peptide thereof or their salts of the present invention can specifically recognize the protein or partial peptide thereof or their salts of the present invention (abbreviated hereinafter as "the protein, etc. of the present invention"), they can be used to quantify the protein, etc. of the present invention in a test solution, particularly by the sandwich immunoassay technique.

Namely, the present invention provides (i) a method for quantifying the protein, etc. of the present invention in a test solution, wherein an antibody to the protein, etc. of the present invention is reacted competitively with a test solution and the labeled protein, etc. of the present invention, and the proportion of the labeled protein, etc. of the present invention that binds to the antibody is measured, and (ii) a method for quantifying the protein, etc. of the present invention in a test solution, wherein a test solution is reacted simultaneously or sequentially with an antibody of the present invention which has been insolubilized on a carrier and a separate labeled antibody of the present invention, and the activity of the labeling agent on the insolubilizing carrier is measured.

In the quantification method of (ii) above, it is desirable that one of the antibodies is an antibody, which recognizes the N terminus of the protein, etc. of the present invention, and the other is an antibody, which reacts to the C terminus of the protein, etc. of the present invention.

It is also possible to assay the protein, etc. of the present invention using monoclonal antibodies to the protein, etc. of the present invention (hereinafter sometimes referred to as "anti-protein antibodies"), or to detect it with a tissue stain, for example. The antibody molecules themselves can be used for this purpose, as can $F(ab')_2$, Fab', or Fab fractions of the antibody molecules.

There are no particular limitations on methods of quantifying the protein, etc. of the present invention using the antibodies of the present invention, and any measurement method may be used as long as it is capable of detecting by chemical or physical means a quantity of antibody, antigen or antibody-antigen complex corresponding to the actual quantity of antigen (such as the amount of protein) in the measured solution, and of calculating said quantity from a standard curve prepared using a standard solution containing a known quantity of the antigen. Examples of suitable methods include nephelometric, competitive binding, immunometric and sandwich methods, with the last-mentioned sandwich method being used preferably because of its sensitivity and specificity.

The labeling agent used in methods which employ labeling may be for example a radioactive isotope, enzyme, fluorescent substance, luminous substance or the like. Radioactive isotopes that can be used include for example $^{125}I$, $^{131}I$, $^{3}H$ or $^{14}C$. Enzymes should be used that are stable and have high specific activity, such as β-galactosidase, β-glucosidase, alkaliphosphatase, peroxidaseormalate dehydrogenase. The fluorescent substances include for example fluorescamine or fluorescein isothiocyanate. The luminous substances include for example luminol, luminol derivatives, luciferin or lucigenin. It is also possible to use a biotin-avidin system to bind the antibody or antigen to the labeling agent.

The antigen or antibody can be insolubilized either by physical adsorption or by a method employing chemical binding which is used to insolubilize or immobilize ordinary proteins or enzymes or the like. Examples of possible carriers include agarose, dextran, cellulose and other insoluble polysaccharides and polystyrene, polyacrylamide, silicon and other synthetic resins as well as glass and the like.

In the sandwich method; an insolubilized monoclonal antibody of the present invention is reacted with a test solution (primary reaction), then with a different, labeled monoclonal antibody of the present invention (secondary reaction), and the quantity of the protein, etc. of the present invention in the test solution can then be quantified by measuring the activity of the labeling agent on the insolubilizing carrier. The order of the primary and secondary reactions can be reversed, and they can be performed simultaneously or with time in between. The labeling agent and insolubilizing method canb as described above. In immunoassay according to the sandwich method, the antibodies used for the solid-phase antibody and the labeled antibody do not necessarily need to be of one type, and a mixture of two or more types of antibodies may be used in order to improve measurement sensitivity, for example.

In the method of the present invention of measuring the protein, etc. of the present invention by the sandwich method, the monoclonal antibodies used in the primary and secondary reactions should preferably be ones that bind to the protein, etc. of the present invention at different sites. That is, as for the antibodies used in the primary and;second reactions, if the antibody used in the secondary reaction recognizes the C terminus of the protein, etc. of the present invention, then an antibody should be used for the primary reaction which recognizes a site other than the C terminus, such as the N terminus for example.

The monoclonal antibodies of the present invention may be used in an assay system other than the sandwich method, such as for example the competitive binding, immunometric or nephelometric method.

In the competitive binding method, the antigen in the test solution and a labeled antigen are reacted competitively with the antibody, unreacted labeled antigen (F) is separated from labeled antigen (B) which is bound to the antibody (B/F separation), and the quantity of antigen in the test solution is quantified by measuring the labeled quantity of either B or F. This reaction method employs soluble antibodies, and polyethylene glycol is used for B/F separation, but other methods include a liquid phase method, in which employs a second antibody to the aforementioned antibody, a solid phase method in which a solid phase antibody is used as the first antibody, and a solid phase method in which a soluble antibody is used as the first antibody and a solid phase antibody as the second antibody.

The immunometric method involves the competitive reaction of an antigen in a test solution and a solid phase antigen with a fixed quantity of labeled antibody, followed by separation of the solid and liquid phases, or else reaction of an excess quantity of antigen in a test solution with a labeled antibody, followed by addition of solid phase antigen and binding of unreacted labeled antibody with the solid phase, after which the solid and liquid phases are separated and the quantity of antigen is quantified in the test solution by measuring the labeled quantity in either phase.

Nephelometry involves measuring the quantity of insoluble precipitate produced by an antigen-antibody reaction in a gel or solution. Laser nephelometry employing laser scattering is suitably used for the cases when there is very little antigen in the test solution, and only a tiny amount of precipitate is obtainable.

No special conditions or operations are needed when applying any one of these immunological measurement methods to the assay of the present invention. A measurement system for the protein, etc. of the present invention can be constructed using the normal conditions and operations for each method along with the ordinary technical skill. Details of these ordinary technical mean can be found in outlines and books such as Irie, Hiroshi Ed., *Radioimmunoassay* (Kodansha, 1974), Irie, Hiroshi Ed., *Radioimmunoassay Continued* (Kodansha, 1979), Ishikawa, Eiji et al Ed. *Enzyme Immunoassay* (Igaku Shoin, 1978), Ishikawa, Eiji et al Ed., *Enzyme Immunoassay* ($2^{nd}$ Edition) (Igaku Shoin, 1982), Ishikawa, Eiji et al Ed., *Enzyme Immunoassay* ($3^{rd}$ Edition) (Igaku Shoin, 1987), *Methods in Enzymology*

Vol. 70, *Immunochemical Techniques (Part A)*, Vol. 73, *Immunochemical Techniques (Part B)*, Vol. 74, *Immunochemical Techniques* (Part C), Vol. 84, *Immunochemical Techniques (Part D: Selected Immunoassays)*, Vol. 92, *Immunochemical Techniques (Part E: Monoclonal Antibodies and General Immunoassay Methods)*, Vol.121, and *Immunochemical Techniques (Part I: Hybridoma Technology and Monoclonal Antibodies)* (Academic Press).

In this way, the protein, etc. of the present invention can be quantified with high sensitivity using the protein antibodies of the present invention.

Moreover, by using the antibodies of the present invention the quantification of concentrations of the protein, etc. of the present invention, it is possible to diagnose a variety of diseases in which the protein, etc. of the present invention is involved (such as oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and other cancers).

Specifically, when increased concentrations of the protein, etc. of the present invention are detected in a patient, a high probability of cancer that is resistant to anti-cancer agents or radiation therapy can be diagnosed. It is also possible to assess susceptibility to anti-cancer agents by investigating the expression of the protein, etc. of the present invention in a cancer patient.

On the other hand, if decreased concentrations of the protein, etc. of the present invention are detected in a patient, a high probability of a disease such as cancer can be diagnosed.

Thus, the antibodies of the present invention are useful in the diagnosis of the aforementioned conditions.

Moreover, the antibodies of the present invention can be used to detect the protein, etc. of the present invention in test samples such as body fluid and tissue. They can also be used for example to produce an antibody column for purifying the protein, etc. of the present invention, or to detect the protein, etc. of the present invention in each fraction during purification.

(4) Drugs Comprising Antibodies of the Present Invention

Of the antibodies of the present invention, those antibodies which can bind to the protein, etc. of the present invention and neutralize ribonucleotide reductase or other enzyme activity involved in nucleic acid metabolism of the protein of the present invention are capable of inhibiting such enzyme activity of the protein of the present invention, and can therefore be used as pharmaceuticals for treatment of diseases such as cancer (including oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and the like).

Drugs for treatment of such conditions comprising the antibodies of the present invention can be administered orally or parenterally to mammals (such as humans, rats, rabbits, sheep, pigs, cows, cats, dogs, monkeys and the like) in a suitable form as pharmaceutical compositions.

The dose varies depending on the target disease, the subject, the symptoms and the route of administration, etc., but for example when used for treatment of cancer in adults, a single dose of an antibody which neutralizes the ribonucleotide reductase or other enzyme activity involved in nucleic acid metabolism of the protein, etc. of the present invention might ordinarily be about 0.01–20 mg/kg, preferably about 0.1–10 mg/kg, more preferably about 0.1–5 mg/kg body weight, administered about 1–5 times a day or preferably about 1–3 times daily by intravenous injection. Equivalent quantities can be administered in the case of other parenteral or oral forms of administration. When symptoms are particularly severe, the dosage can be increased correspondingly.

An antibody of the present invention which neutralizes the ribonucleotide reductase or other enzyme activity involved in nucleic acid metabolism of the protein of the present invention can be administered either by itself or in a suitable pharmaceutical composition. Pharmaceutical compositions used in such administration include pharmacologically acceptable carriers, diluents and excipients. Such compositions are provided in a form suitable for oral or parenteral administration. For example, a composition for oral administration might be in a solid or liquid form, such as tablets (including sugar-coated and film-coated tablets), pills, granules, powder, capsules (including soft capsules) syrup, emulsion or suspension. Such compositions are manufactured by publicly known methods, and contain carriers, diluents and excipients, which are ordinarily used in pharmaceutical formulation. For example, carriers and excipients that can be used in tablets include lactose, starch, sucrose and magnesium stearate.

Compositions for parenteral administration include for example injections and suppositories, and injections include intravenous injections, subcutaneous injections, intradermic injections, intramuscular injections and drip injections. Such injections are prepared by publicly known methods, such as for example by dissolving, suspending or emulsifying the antibody in a sterile aqueous or oily liquid which is ordinarily used for injections. Injectable aqueous liquids include for example physiological saline and isotonic liquids containing glucose or other adjuvants, and can be used in combination with suitable solubilizers such as alcohols (e.g. ethanol), polyalcohols (e.g. propylene glycol, polyethylene glycol) and nonionic surfactants (e.g. polysorbate 80, HCO-50 (polyoxyethylene (50 mol) adduct of hydrogenated castor oil)). Oily liquids include for example sesame or soy bean oil, which can be used in combination with solubilizers such as benzyl benzoate and benzyl alcohol. The prepared injection is normally packed in a suitable ampoule. Suppositories for rectal administration are prepared by mixing the antibody or a salt thereof with an ordinary suppository base.

The aforementioned oral or parenteral pharmaceutical compositions should be prepared in a unit dosage form suited to the dosage of the active ingredient. Examples of unit dosage forms include tablets, pills, capsules, injections (ampoules) and suppositories. Such unit dosage forms ordinarily contain 5–500 mg of the antibody, or more specifically 5–100 mg in the case of an injection and 10–250 mg in the case of other dosage forms.

The compositions mentioned above may also contain other active ingredients as long as combination with the antibody does not result in any undesirable interactions.

(5) Screening Drug Candidate Compounds for Various Diseases

Compounds or salts thereof which promote the enzyme activity of the protein of the present invention (e.g. ribonucleotide reductase or other enzyme activity related to nucleic acid metabolism) can be used as pharmaceuticals for prevention, etc. of various diseases such as cancer (including oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and the like).

On the other hand, compounds or salts thereof which inhibit the enzyme activity of the protein of the present invention can be used as pharmaceuticals for treatment, etc. of various diseases such as cancer (including oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and the like).

Consequently, the protein, etc. of the present invention is useful as a reagent for screening compounds or salts thereof which promote or inhibit the enzyme activity of the protein of the present invention.

Namely, the present invention provides a method for screening ribonucleotide reductase (RR) promoters and RR inhibitors, involving a comparison of (i) contact of the protein, etc. of the present invention with a substrate and (ii) contact of the protein of the present invention and with a substrate and a test compound.

Specifically, the aforementioned screening method might be characterized for example by measurement and comparison of the RR activity of the protein of the present invention in situations (i) and (ii).

Any substrate can be used which is a suitable substrate for the protein, etc. of the present invention, and ribonucleotide-2-phosphate is ordinarily used. Ribonucleotide with a radioactive label (e.g. $^{14}C$, $^{3}H$) and the like is preferred for the ribonucleotide-2-phosphate.

Examples of test compounds include peptides, proteins, non-peptidergic compounds, synthetic compounds, fermentation products, cell extracts, plant extracts, animal tissue extracts and plasma. These compounds may be novel compounds or publicly known compounds.

To implement this screening method, samples of the protein, etc. of the present invention are prepared by suspending the protein, etc. of the present invention in a buffer suitable for screening. The buffer may be any buffer with a pH of about 4–10 (preferably about 6–8) which does not inhibit binding between the protein, etc. of the present invention and the substrate, such as a phosphate buffer or Tris-hydrochloric acid buffer.

The ribonucleotide reductase or other enzyme activity related to nucleic acid metabolism of the protein, etc. of the present invention can be quantified according to publicly known methods.

For example, if the RR activity in (ii) above is promoted by roughly at least 20%, more preferably at least 30%, most preferably at least 50% in comparison with (i) above, the test compound can be identified as one that promotes the RR activity of the protein, etc. of the present invention. Conversely, if for example the RR activity in (ii) above is in inhibited by roughly at least 20%, preferably at least 30%, more preferably at least 50% in comparison with (i) above, the test compound can be identified as one that inhibits the RR activity of the protein of the present invention.

The screening kit of the present invention is one that contains the protein, etc. of the present invention. Examples of the screening kit of the present invention are given in Example 1 and Example 2 below.

EXAMPLE 1

Screening Reagent (1) Measurement Buffer
  50 mM Hepes buffer (pH 7.2), 6 mM dithiothreitol, 4 mM magnesium acetate, 4 mM ATP, 5 units/ml NDP kinase (2) Protein Sample
  The protein or salt thereof of the present invention (3) Substrate
  [$^{14}C$]-CDP or [$^{3}H$]-CDP (4) Detection
  Measurement of radioactivity with a liquid scintillation counter

[Measurement Method]

The test compound is added to a reaction mixture containing 100 pmol [$^{14}C$]-CDP or [$^{3}H$]-CDP, the protein or salt thereof of the present invention, 50 mM Hepes buffer (pH 7.2), 6 mM dithiothreitol, 4 mM magnesium acetate, 4 mM ATP and 5 units/ml NDP kinase, which is warmed for 30 minutes at 37° C. and then heated for 5 minutes in a boiling water bath (100° C.). This is then added to a reaction mixture comprising 90 mM Hepes buffer (pH 6.6), 10 mM magnesium chloride, 0.2 mM dNTP, 5 units Klenow fragment, 1 μg/μl DNA (salmon-derived DNA digested with Hae III) and 150 ng/μl 6-mer random primer, and reacted for 30 minutes at room temperature. The reaction mixture is then spotted on filter papers (Whatman DE-81), air-dried, washed three times in a 5% sodium phosphate solution and once in a 95% ethanol solution and then dried. Radioactivity on the filter papers is then measured with a liquid scintillation counter.

EXAMPLE 2

Screening Reagent (1) Cells
  MCF7 cells (2) DNA Damage Inducer
  Adriamycin (3) Ribonucleotide Reductase Substrate
  [$^{3}H$]-CDP (4) Detection
  Measurement by liquid scintillation counter of [$^{3}H$]-dCTP radioactivity incorporated into the DNA (Measurement Method)

Adriamycin (0.2 μg/ml) is injected into MCF7 cells, and after 2 days' incubation the permeability of the cell membrane is enhanced by treatment with L-lysophosphatidil choline. A reaction mixture containing the test compound is then added, followed by [$^3$H]-CDP, and incubated at 37° C. for 15 minutes. The cells are harvested with a cell harvester, and radioactivity incorporated into the DNA is measured.

The compounds and salts thereof obtained using the screening method or screening kit of the present invention are selected from the test compounds (such as peptides, proteins, non-peptidergic compounds, synthetic compounds, fermentation products, cell extracts, plant extracts and animal tissue extracts), and are those compounds which promote or inhibit the ribonucleotide reductase or other enzyme activity related to nucleic acid metabolism of the protein, etc. of the present invention. These compounds maybe novel compounds or publicly known compounds.

Salts with physiologically acceptable acids (such as inorganic or organic acids) or bases (such as alkali metals) may be used as the salts of these compounds, and physiologically acceptable acid-added salts are particularly desirable. For example, salts with inorganic acids (such as hydrochloric acid, phosphoric acid, hydrobromic acid or sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid or benzenesulfonic acid) may be used.

The compounds or salts thereof which inhibit the enzyme activity of the protein of the present invention are,useful as pharmaceuticals such as safe and low toxic pharmaceuticals for the treatment various diseases including cancer.

The compounds or salts thereof which promote the enzyme activity of the protein of the present invention are useful as pharmaceuticals such as safe and low toxic pharmaceuticals for the prevention of various diseases including cancer.

Ordinary methods may be followed when a compound obtained using the screening method or screening kit of the present invention is used as a pharmaceutical as described above. For example, as in the case of a pharmaceutical containing the protein, etc. of the present invention as described above, a tablet, capsule, elixir, microcapsule, sterile solution or suspension form may be used.

Because the thus-obtained preparation is safe and low toxic, it can be administered to mammals (including for example humans, mice, rats, rabbits, sheep, pigs, cows, horses, cats, dogs, monkeys or chimpanzees).

The dose of the compound or salt thereof varies depending on the target disease, the subject and the route of administration, etc., but for example, when a compound which inhibits the enzyme activity of the protein of the present invention is administered orally for treatment of cancer, the dose is normally about 0.1–100 mg, preferably about 1.0–50 mg, or more preferably about 1.0–20 mg per day for adults (as 60 kg body weight). In parenteral administration, the single dose of the protein, etc. varies depending on the subject, the target disease and so forth, but for example, when a compound which inhibits the enzyme activity of the protein of the present invention is administered for treatment of cancer in the form of an injection, it is advantageous to administer, for example, a daily dose of about 0.01–30 mg, preferably about 0.1–20 mg, or more preferably about 0.1–10 mg for adults (as 60 kg body weight). For other animal species, the corresponding dose as converted per 60 kg weight can be administered.

On the other hand, when a compound which promotes the enzyme activity of the protein of the present invention is administered orally for prevention of cancer, the dose is normally about 0.1–100 mg, preferably about 1.0–50 mg, or more preferably about 1.0–20 mg per day for adults (as 60 kg body weight). In parenteral administration, the single dose of the protein, etc. varies depending on the subject, the target disease and so forth, but for example, when a compound which promotes the enzyme activity of the protein of the present invention is administered for prevention of cancer in the form of an injection, it is advantageous to administer, for example, a daily dose of about 0.01–30 mg, or preferably about0.1–20 mg, or more preferably about 0.1–10 mg for adults (as 60 kg body weight). For other animal species, the corresponding dose as converted per 60 kg weight can be administered.

(6) Drugs Comprising Antisense Oligonucleotides

Antisense oligonucleotides which are complementary to DNA or mRNA encoding the protein of the present invention, and which can suppress expression of the protein, etc. of the present invention, can suppress the function of the protein, etc. of the present invention as it is expressed in the body as described above. Consequently, such antisense oligonucleotides can be used as pharmaceuticals such as pharmaceuticals for treatment, etc. of cancer and other diseases.

When these antisense oligonucleotides are used as such pharmaceuticals, they can be manufactured in the same way as the aforementioned pharmaceuticals for prevention of various diseases which contain the DNA of the present invention, and administered to mammals.

For example, when using such antisense oligonucleotides, they can be administered alone or inserted into a suitable retrovirus vector, adenovirus vector, adenovirus-associated virus vector or the like and administered according to ordinary means. Such antisense oligonucleotides can be prepared by themselves or together with an adjuvant or other physiologically acceptable carrier for purposes of easy ingestion, and administered with a gene gun or hydrogel catheter or other catheter.

Such antisense oligonucleotides can also be used as diagnostic oligonucleotide probes to investigate the existence and expression of the DNA of the present invention in tissue or cells.

(7) DNA-Transferred Animals

The present invention provides non-human mammals having foreign DNA encoding the protein, etc. of the present invention (abbreviated hereinafter as "foreign DNA of the present invention") or modified DNA thereof (sometimes abbreviated hereinafter as "modified foreign DNA of the present invention"). Specifically, there are provided:

(1) Non-human mammals having foreign DNA or modified DNA thereof of the present invention;

(2) The animals described in (1) above, wherein the non-human mammals are rodents;

(3) The animals described in (2) above, wherein the rodents-are mice or rats;

(4) A recombinant vector or the like which can be expressed in mammals, comprising foreign DNA or modified DNA thereof of the present invention.

The non-human mammals having the foreign DNA or modified DNA thereof of the present invention (hereinafter abbreviated as "DNA-transferred animals of the present invention") can be-prepared by transferring the target DNA by a method such as the calcium phosphate method, electrical pulse method, lipofection method, agglutination method, microinjection method, particle gun method or DEAE-dextran method into germ cells and the like including unfertilized eggs, fertilized eggs, sperm and primordial cells thereof, preferably during the embryonic stage of non-human mammalian development (and more preferably during the single-cell or fertilized egg cell stage, generally before the eight-cell stage). Such DNA transferring methods can also be used to transfer the desired foreign DNA of the present invention into somatic cells, living organs or tissue cells and to culture the cells or tissue, and the DNA-transferred animals of the present invention can also be created by fusing these cells with the aforementioned germ cells according to publicly known cell fusion methods.

Non-human mammals that can be used include for example cows, pigs, sheep, goats, rabbits, dogs, cats, guinea pigs, hamsters mice and rats. From the standpoint of preparing animal disease models, rodents are preferred which have relatively short ontogenies and life cycles and which are easy to breed, especially mice (including pure strains such as C57BL/6 and DBA2 and hybrid strains such as B6C3F1, BDF1, B6D2F1, BALB/c and ICR) and rats (such as Wistar and SD rats).

In the context of recombinant vectors, which can be expressed in mammals, the term "mammal" applies to humans as well as non-human mammals.

The foreign DNA of the present invention is DNA of the present invention that has been previously isolated and extracted from mammals, not DNA of the present invention which is already present in the non-human mammals.

The modified DNA of the present invention may be for example DNA in which modifications (such as mutations) have occurred in the original base sequence of the DNA of the present invention, including specifically DNA with bases added, deleted or substituted with other bases, or it may be abnormal DNA.

DNA, which expresses an abnormal protein of the present invention can be used as the abnormal DNA, including DNA which expresses a protein which inhibits the function of the normal protein of the present invention.

The foreign DNA of the present invention may be from mammals of either the same species or different species from the target animals. When transferring the DNA of the present invention into the target animals, it is generally advantageous to use a DNA construct having the DNA ligated downstream from a promoter which can be expressed in animal cells. For example, when transferring human DNA of the present invention, a DNA-transferred mammal can be prepared which strongly expresses the DNA of the present invention by microinjecting into the fertilized eggs of the target mammal, such as fertilized mouse eggs, a DNA construct (such as a vector) having the human DNA of the present invention ligated downstream from various promoters which can express DNA derived from various mammals (such as rabbits, dogs, cats, guinea pigs, hamsters, rats or mice) having DNA of the present invention which is highly homologous to the human DNA.

Plasmids derived from *E. coli, B. subtilis* or yeast, bacteriophages such as λ-phage, retroviruses such as Moloney leukemia virus and animal viruses such as vaccinia virus and baculovirus may be used as the manifestation vector of the protein of the present invention. Among them, plasmids derived from *E. coli, B. subtilis* or yeast are preferred.

Promoters that can be used to regulate DNA expression include for example (1) DNA promoters derived from viruses (such as simian virus, cytomegalovirus, Noloney leukemia virus, JC virus, mammary tumor virus or polio virus), and (2) promoters derived from various mammals (humans, rabbits, dogs, cats, guinea pigs, hamsters, rats, mice, etc.) or birds (chickens, etc.), such as albumin, insulin II, uroplakin II, elastase, erythropoietin, endothelin, muscle creatine kinase, glial fibrillary acidic protein, glutathione S-transferase, platelet derived growth factor β, keratin K1, K10 and K14, collagen Type I and Type II, cyclic AMP-dependent protein kinase βI subunit, dystrophin, tartaric acid-resistant alkali phosphatase, cardiac sodium diuretic factor, endothelial receptor tyrosine kinase (normally abbreviated as Tie2), sodium-potassium ATPase (Na,K-ATPase), neurofilament light chain, metallothionein I and IIA, tissue inhibitor of metalloproteinase-1, MHC class I antigen (H-2L), H-ras, renin, dopamine β-hydroxylase, thyroid peroxidase (TPO), polypeptide chain elongation factor 1α (EF-1α), β-actin, α- and β-myosin heavy chains, myosin light chains 1 and 2, myelin basic protein, thyroglobulin, Thy-1, immunoglobulin, H chain variable region (VNP), serum amyloid P component, myoglobin, troponin C, smooth muscle α-actin, preproenkephalin A, vasopressin and other promoters. Particularly suitable are cytomegalovirus promoter, human polypeptide chain elongation factor 1α (EF-1α) promoter and human and chicken β-actin promoters, which are capable of strong expression throughout the body.

The aforementioned vectors should preferably have the sequence (generally called the terminator) which completes transcription of the target mRNA in DNA-transferred mammals. Various DNA sequences derived from viruses, mammals and birds can be used, and the simian-virus SV40 terminator is used preferably.

In order to achieve greater expression of the desired foreign DNA, it is also possible depending on the purpose to attach various DNA splicing signals, enhancer regions or parts of eukaryote-derived DNA introns either 5' upstream from the promoter region, between the promoter region and the translation region or 3' downstream from the translation region.

Translation regions for the normal protein of the present invention may be obtained as all or part of DNA derived from the livers, kidneys, thyroid glands or fibroblast cells of various mammals (such as humans, rabbits, dogs, cats, guinea pigs, hamsters, rats, mice, etc.) or genome DNA from various commercial genomic DNA libraries, or may be obtained from a stock of complement DNA prepared by publicly known methods from mRNA derived from livers, kidneys, thyroid glands or fibroblast cells. In the case of abnormal foreign DNA, mutated translation regions can be prepared by point mutagenesis of the translation regions of normal proteins obtained from the aforementioned cells or tissue.

Such translation regions can be prepared as DNA constructs capable of expression in transgenic animals by conventional genetic engineering methods of attachment downstream from the aforementioned promoter, or if desired, upstream from the terminator site.

Introduction of the foreign DNA of the present invention at the fertilized egg cell stage ensures that the foreign DNA of the present invention will be present in all germ and somatic cells of the target mammal. The presence of the foreign DNA of the present invention in the animal is germ cells after DNA introduction means that all the animal's progeny will retain the foreign DNA of the present invention in all their germ and somatic cells. The offspring of animals of this species that inherit the foreign DNA of the present invention will have the foreign DNA of the present invention in all their germ and somatic cells.

Non-human mammals in which normal foreign DNA of the present invention has been transferred can be bred to confirm stable retention of the foreign DNA of the present invention, and can be successively reared in a normal environment as animal hosts of such DNA.

Introduction of the foreign DNA of the present invention at the fertilized egg cell stage ensures that the foreign DNA of the present invention will be present in excess in all germ and somatic cells of the target mammal. The presence of an excess of the foreign DNA of the present invention in the animal's germ cells after DNA introduction means that all the animal's progeny will retain an excess of the foreign DNA of the present invention in all their germ and somatic cells. The offspring of animals of this species that inherit the foreign DNA of the present invention will have an excess of the foreign DNA of the present invention in all their germ and somatic cells. It is possible to obtain homozygotic animals with the introduced DNA in both homologous chromosomes, and breed male and female so that all the progeny have this DNA in excess.

The normal DNA of the present invention is strongly expressed in non-human mammals having normal foreign DNA of the present invention, and promotion of the function of the intrinsic normal DNA results ultimately in hyperfunction of the protein of the present invention, making these animals useful as disease models. For example, the normal DNA-transferred animals of the present invention can be used to elucidate the pathology of hyperfunction of the protein of the present invention and other diseases related to the protein of the present invention, and to investigate therapies for these conditions.

Furthermore, since mammals in which the normal foreign DNA of the present invention has been transferred have symptoms of increased free protein of the present invention, it can also be used in screening tests for pharmaceuticals for treatment of conditions related to the protein of the present invention.

Non-human mammals having abnormal foreign DNA of the present invention can be bred to confirm stable retention of the foreign DNA, and can be successively reared in a normal environment as animal hosts of such DNA. Furthermore, the target foreign DNA can be incorporated into one of the aforementioned plasmids and used as a raw material. A DNA construct with a promoter can be created according to ordinary genetic engineering techniques. Transposition of the abnormal DNA of the present invention at the fertiliz d egg stage ensures that the abnormal DNA of the present invention is present in all the germ and somatic cells of the target mammal. The presence of the abnormal DNA of the present invention in the animal's germ cells after DNA introduction means that all the animal's progeny will retain the abnormal DNA of the present invention in all their germ and somatic cells. The offspring of animals of this species that inherit the foreign DNA of the present invention will have the abnormal DNA of the present invention in all their germ and somatic cells. It is possible to obtain homozygote animals with the introduced DNA in both homologous chromosomes, and breed male and female so that all the progeny have this DNA.

The abnormal DNA of the present invention is strongly expressed in non-human mammals having abnormal foreign DNA of the present invention, and inhibition of the function of the intrinsic normal DNA can ultimately result in inactive dysfunction of the protein of the present invention, making these animals useful as disease models. For example, it is possible to use the abnormal DNA-transferred animals of the present invention to elucidate the pathology of inactive dysfunction of the protein of the present invention, and to investigate therapies for this condition.

In terms of specific possible applications, an animal that strongly expressed abnormal foreign DNA of the present invention could be a model for elucidating inhibition of normal protein function (dominant negative effect) caused by the abnormal protein of the present invention in inactive dysfunction of the protein of the present invention. Moreover, since mammals with transferred abnormal foreign DNA of the present invention have symptoms of increased free protein of the present invention, they can be used in screening tests for pharmaceuticals for treatment of inactive dysfunction of the protein of the present invention.

Other applicability for the aforementioned two types of DNA-transferred animals of the present invention include:

(1) As cell sources for tissue culture;

(2) In direct analysis of DNA or RNA in the tissue of DNA-transferred animals of the present invention or analysis of proteins in tissue to elucidate connections with proteins that are specifically expressed or activated by the protein of the present invention;

(3) In researching the function of cells from tissue which is generally difficult to culture using cells from tissue having the DNA of the present invention, when such cells can be cultured by standard tissue culture techniques;

(4) In screening for pharmaceuticals that enhance the function of cells using the cells described in (3) above; and (5) In isolation and purification of modified protein of the present invention, and production of antibodies thereto.

DNA-transferred animals of the present invention could also be used to investigate the clinical symptoms of diseases related to the protein of the present invention, including inactive dysfunction of the protein of the present invention, to obtain more detailed pathological findings from various organs of disease models related to the protein of the present invention, to develop new therapies, and to contribute to research and therapies for secondary conditions stemming from such diseases.

It is also possible to remove various organs from the DNA-transferred animals of the present invention, cut them up, use a protease such as trypsin to obtain free DNA-transferred cells, and prepare a cell line from the culture or cultured cells. By allowing cells that produce the protein of the present invention to be specified and their nucleic acid metabolic regulation function investigated along with abnormalities therein, these animals also provide an effective research tool for understanding the protein of the present invention and action thereof.

Moreover, the DNA-transferred animals of the present invention might also be used to provide a rapid method of screening pharmaceuticals in the development of treatments for of diseases related to the protein of the present invention, including inactive dysfunction of the protein of the present invention, using the testing and assay methods described above. The DNA-transferred animals of the present invention or vectors expressing foreign DNA of the present invention could also be used to investigate and develop DNA therapies for diseases related to the protein of the present invention.

(8) Knockout Animals

The present invention provides non-human mammals embryonic stem cells in which the DNA of the present invention is inactivated, and non-human mammals that fail to express the DNA of the present invention. Specifically, there are provided:

(i) Non-human mammal embryonic stem cells in which the DNA of the present invention is inactivated;
(ii) The embryonic stem cells described in (i) above, wherein the DNA is inactivated by introduction of a reporter gene (such as the E. coli β-galactosidase gene);
(iii) The embryonic stem cells described in (i) above which are neomycin resistant;
(iv) The embryonic stem cells described in (i) above, wherein the non-human mammal is a rodent;
(v) The embryonic stem cells described in (ii) above, wherein the rodent is a mouse;
(vi) A non-human mammal, which fails to express the DNA of the present invention, in which said DNA has been inactivated;
(vii) The non-human mammal described in (vi) above, wherein the DNA is inactivated by introduction of a reporter gene (such as the E. coli β-galactosidase gene), and the reporter gene can be expressed under the control of a promoter for the DNA of the present invention.
(viii) The non-human mammal described in (vi) above, wherein the non-human mammal is a rodent;
(ix) The non-human mammal described in (viii) above, wherein the rodent is a mouse; and
(x) A screening method for compounds or salts thereof which promote or inhibit promoter activity for the DNA of the present invention, wherein a test compound is administered to the animal described in (vii) above, and expression of the reporter gene is detected.

Non-human mammal embryonic stem cells in which the DNA of the present invention is inactivated are the embryonic stem cells (abbreviated hereinafter as "ES cells") of non-human mammals wherein either DNA expression ability is suppressed by the addition of an artificial modification to the DNA of the present invention in the non-human mammal, or where in the activity of the protein of the present invention encoded by said DNA has effectively been eliminated so that the DNA is effectively incapable of expressing the protein of the present invention (sometimes referred to hereinafter as the knockout DNA of the present invention).

The animals that can be used as the non-human mammal are the same as those described above.

Methods for artificially modifying the DNA of the present invention include for example using genetic engineering techniques to delete all or part of the DNA sequence, or to insert or substitute other DNA. The knockout DNA of the present invention is produced when these modification result in displacement of the codon reading frame or disruption of the function of the promoter or exon.

Specific examples of non-human mammal embryonic stem cells in which the DNA of the present invention is inactivated (abbreviated hereinafter as ES cells of the present invention comprising inactivated DNA or knockout ES cells of the present invention) include those in which the DNA of the present invention in the target non-human mammal is isolated, a drug-resistant gene of which typical examples are neomycin-resistant, hygromycin-resistant or other drug-resistant genes, or a reporter gene or the like of which typical examples are lacZ (β-galactosidase gene) or cat (chloramphenicol acetyltransferase gene), is inserted into the exon to disrupt the function of the exon, or else a DNA sequence (such as polyA addition signal) which terminates gene transcription is inserted into the intron between the exons to completely prevent mRNA synthesis, and ultimately a DNA chain having a DNA sequence constructed to disrupt genes (abbreviated hereinafter as "the targeting vector") is introduced into the chromosomes of the animal by homologous recombination, for example. The knockout ES cells of the present invention can be selected by analyzing the resulting ES cells either by the southern hybridization method using a DNA sequence on or near the DNA of the present invention as a probe, or by the PCR method using as primers a DNA sequence on the targeting vector and a DNA sequence of a nearby region other than the DNA of the present invention used in creating the targeting vector.

For the original ES cells used to inactivate the DNA of the present invention by homologous recombination or the like, it is possible to use already established cells as described above, or to establish new ones according to the publicly known Evans and Kaufman methods. For example, 129 mouse ES cell lines are currently in general use, but since the immunological background is unclear, a good way to establish a pure line for which the immunological and genetic background is known would be to use C57BL/6 mice or else BDF1 mice (F1 of C57BL/6 and DBA/2) in which the low ovum collection of C57BL/6 mice has been improved by cross-breeding with DBA/2 mice. Not only do BDF1 mice have high ovum collection and sturdy ova, but since they are based on C57BL/6 mice, the genetic background of ES cells obtained therefrom can be restored by back crossing with C57BL/6 mice when preparing a disease model mouse.

The blastocyst 3.5 days after fertilization is generally used in establishing ES cells, but many early embryos can be obtained efficiently by collecting 8-cell embryos and culturing them to the blastocyst stage.

Either female or male ES cells can be used, but generally male ES cells are more useful for preparing reproductive lineage chimeras. Females and males should be distinguished as quickly as possible to reduce the work of complex cultures.

One method of distinguishing female and male ES cells is to use PCR to amplify and detect the genes of the sex determining region of the Y chromosome. At one time about $10^6$ cells were required for karyotype analysis, but this method uses only about one colony's worth of ES cells (about 50 cells), allowing primary selection of ES cells by sexing the cells at the initial culture stage. This greatly reduces the work of the initial culture stage by allowing early selection of male cells.

Secondary selection can be accomplished for example by using the G-banding method to confirm the number of chromosomes. Ideally, 100% of the ES cells should have a normal number of chromosomes, but when this is difficult due to the physical manipulation used in establishing the cells, for example. ES cell should be cloned again into the normal cells (for example, those having the normal mouse chromosome number of 2n=40) after the ES cell genes are knocked out.

The resulting embryonic stem cell line will normally be highly productive, but since it can easily lose the power of ontogenesis, successive cultures must be performed very carefully. For example, culture can be performed in a carbon dioxide incubator (preferably with 5% carbon dioxide, 95% air or 5% oxygen, 5% carbon dioxide, 90% air) at about 37° C. in the presence of LIF (1–10000 U/ml) on suitable feeder cells such as STO fibroblasts. During passage, treatment with a trypsin/EDTA solution (normally 0.001–0.5% trypsin/0.1–5 mM EDTA, preferably about 0.1% trypsin/1 mM EDTA) is used to produce a single cell, which is seeded on a previously prepared feeder cell. Such a passage is normally performed every 1–3 days, and at that time if a cell is found to be morphological abnormal the cultured cells are discarded.

ES cells can be differentiated into a variety of cells types, such as musculus longus capitis, visceral muscle or cardiac muscle cells, by culturing under suitable conditions either in a monolayer culture until they reach high density, or else in a float culture until they form a cell clump (M. J. Evans and M. H. Kaufman, *Nature,* Vol. 292, 154 (1981); G. R. Martin, *Proc. Natl. Acad. Sci. USA,* Vol. 78, 7634 (1981); T. C. Doetschmanetal, *Journal of Embryology and Experimental Morphology,* Vol. 87, 27 (1985). Cells obtained by differentiation of the ES cells of the present invention that fail to express the DNA of the present invention are useful in investigating significance in vitro.

Non-human mammals, which do not express the DNA of the present invention can be distinguished from normal animals by measuring the amount of mRNA by publicly known methods and indirectly comparing the amount expressed.

The same animals mentioned above can be used as these non-human mammals.

In the non-human mammals which do not express the DNA of the present invention, the DNA of the present invention can be knocked out for example by introducing a targeting vector created as described above into mouse embryonic stem cells or mouse egg cells, resulting in the replacement by genetic homologous recombination of the DNA of the present invention on the chromosomes of the mouse's embryonic stem cells or egg cells by a DNA sequence in the targeting vector in which the DNA of the present invention is inactivated.

Cells in which the DNA of the present invention is knocked out can be evaluated either by the southern hybridization method using a DNA sequence on or near the DNA of the present invention as a probe, or by the PCR method using as primers a DNA sequence on the targeting vector and the DNA sequence of a nearby region other than the mouse-derived DNA of the present invention used in creating the targeting vector. When using non-human mammal embryonic stem cells, a cell line in which the DNA of the present invention is inactivated can be cloned by homologous recombination, and the cells injected into the embryos or blastocysts of a non-human mammal at a suitable stage such as the 8-cell stage. The resulting chimera embryo is then transplanted to the uterus of the non-human mammal, which has been made falsely pregnant. The resulting animal is a chimera animal comprising both cells with the normal DNA locus of the present invention and the artificially modified DNA locus of the present invention.

If some of the reproductive cells of this chimera animal have modified DNA of the present invention, individuals all of whose tissues are made up of cells with the artificial modification included in the DNA locus of the present invention can be selected by evaluation of coat color, for example, from a population produced by the breeding of this chimera with a normal individual. The individuals obtained in this way normally are hetero for failure to express the protein of the present invention, and by breeding such animals it is possible to obtain from their offspring individuals that are homo for failure to express the protein of the present invention.

When using egg cells, it is possible to obtain transgenic non-human mammals with the targeting vector inserted into their chromosomes by injecting a DNA solution into the egg cell nucleus with microinjection. These transgenic non-human mammals are obtained by selection of those having mutations to the genetic locus of the present invention with homologous recombination.

Individuals in which the DNA of the present invention has been knocked out in this way can be successively reared in a normal environment after confirmation that the DNA is knocked out in animals obtained by breeding.

Reproductive lineages can also be obtained and maintained by ordinary methods. Namely, female and male animals having the inactivated DNA can be bred to obtain homozygous animals with the inactivated DNA in both homologous chromosomes. The resulting homozygote animals can be efficiently obtained by rearing so that for each mother animal there is one normal individual and multiple homozygote individuals. By breeding female and male heterozygous animals, homozygous and heterozygous animals with the inactivated DNA are successively produced.

Non-human mammal embryonic stem cells in which the DNA of the present invention is inactivated are extremely useful in preparing non-human mammals which do not express the DNA of the present invention.

Moreover, because non-human mammals which do not express the DNA of the present invention lack various kinds of biological activity which may be induced by the protein of the present invention, they can be models for various diseases stemming from inactivation of the biological activity of the protein of the present invention, and are therefore useful in finding the causes and investigating therapeutic methods for such diseases.

(9) A Method for Screening Compounds having therapeutic or Preventive Effects for Diseases Stemming from Defects or Damage, etc. to the DNA of the Present Invention Non-human mammals which do not express the DNA of the present invention can be used to screen compounds having therapeutic or preventive effects for diseases stemming from defects or damage, etc. to the DNA of the present invention (such as oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin-cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and other cancers).

Namely, the present invention provides a screening method for compounds having therapeutic or preventive effects for diseases stemming from defects or damage, etc. to the DNA of the present invention, wherein a test compound is administered to a non-human mammal which does not express the DNA of the present invention, and changes in the animal are observed and measured.

The non-human mammals that do not express the DNA of the present invention which are used in this screening method may be those described previously.

Examples of test compounds include peptides, proteins, non-peptidergic compounds, synthetic compounds, fermentation products, cell extracts, plant extracts, animal tissue extracts and plasma. These compounds may be novel compounds or publicly known compounds.

Specifically, a non-human mammal which does not express the DNA of the present invention is treated with the test compound and compared with an untreated control animal, and the therapeutic and preventative effects of the test compound can be evaluated using changes in the organs, tissues and disease symptoms, etc. of the animal as an index.

Methods for treating the test animal with the test compound include for example oral or intravenous administration, and can be selected as appropriate depending on the symptoms of the test animal and the properties of the test compound. The dosage of the test compound can also be selected as appropriate depending on the method of administration and the properties of the test compound.

For example, when screening a compound with therapeutic or preventative effects against cancer, cancer is induced in non-human mammals which do not express the DNA of the present invention, the test compound is administered before and after cancer induction, and the cancer rate and survival rate of the animals are measured over time.

When a test compound is administered to test animals in this screening method and the survival rate rises about 10% or more or preferably about 30% or more or more preferably about 50% or more, the test compound can be selected as a compound with therapeutic and preventative effects against cancer.

Compounds obtained with the screening method of the present invention are compounds selected from the test compounds described above, and because they have therapeutic and preventative effects against diseases caused by defects or damage, etc. to the protein of the present invention (such as oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and other cancers), they can be used as safe and low toxic pharmaceuticals for the treatment and prevention of such diseases. Moreover, compounds derived from compounds obtained by this screening method can also be used in the same way.

Compounds obtained by this screening method may be in the form of salts. Salts of such compounds which can be used include salts with physiologically acceptable acids (such as inorganic and organic acids) or bases (such as alkali metals), with physiologically acceptable acid addition salts being particularly desirable. For example, salts with inorganic acids (such as hydrochloric acid, phosphoric acid, hydrobromic acid or sulphuric acid) or with organic acids (such as acetic acid, formic acid, propionic acid, fumaric acid, maleic acid, succinic acid, tartaric acid, citric acid, malic acid, oxalic acid, benzoic acid, methanesulfonic acid or benzenesulfonic acid) may be used.

Drugs comprising a compound or salt thereof obtained by this screening method can be manufactured in the same way as the previously described pharmaceuticals comprising the protein of the present invention.

Because preparations obtained in this way are safe and of low toxicity, they can be administered safely for example to mammals (such as humans, rats, mice, guinea pigs, rabbits, sheep, pigs, cows, horses, cats, dogs, monkeys, etc.).

The dosage of the compound or salt thereof depends on the target disease, subject and route of administration, but for example when such a compound is administered orally for prevention of cancer, the dose is normally about 0.1–100 mg, or preferably about 1.0–50 mg, or more preferably about 1.0–20 mg per day for adults (as 60 kg body weight). In parenteral administration, the single dose of the compound varies depending on the subject, the target disease and so forth, but for example when said compound is administered for prevention of cancer in the form of an injection, it is advantageous to administer, for example, a daily dose of about 0.01–30 mg, or preferably about 0.1–20 mg, or more preferably about 0.1–10 mg for adults (as 60 kg body weight) by intravenous injection. For other animal species, the corresponding dose as converted per 60 kg weight can be administered.

(10) A Method of Screening Compounds which Promote or Inhibit the Activity of Promoters for the DNA of the Present Invention The present invention provides a screening method for compounds or salts thereof which promote or inhibit the activity of promoters for the DNA of the present invention, wherein a test compound is administered to a non-human mammal which does not express the DNA of the present invention, and the expression of a reporter gene is detected.

In this screening method, the non-human mammal which does not express the DNA of the present invention is one in which the DNA of the present invention has been inactivated by introduction of a reporter gene, and the reporter gene can be expressed under the control of a promoter for the DNA of the present invention.

The test compounds may be the same as those described above.

The reporter gene may be as described above, with the β-galatosidase gene (lacZ) being particular suitable.

In a non-human mammal which does not express the DNA of the present invention in which the DNA of the present invention has been replaced by a reporter gene, since the reporter gene is under the control of a promoter for the DNA of the present invention, the activity of the promoter can be detected by tracing the expression of the protein encoded by the reporter gene.

For example, when part of the DNA region encoding the protein of the present invention has been replaced by an *E. coli*-derived β-galactosidase gene (lacZ), β-galactosidase is expressed instead of the protein of the present invention in tissue in which the protein of the present invention would ordinarily be expressed. Consequently, staining with a reagent such as 5-bromo-4-chloro-3-indolyl-β-galactopyranoside (X-gal) which forms a substrate for β-galactosidase is a simple way of observing the expression of the protein of the present invention in a living body of animal. Specifically, a mouse lacking the protein of the present invention or a tissue section thereof is fixed with glutaraldehyde or the like and washed with Dulbecco's phosphate buffered saline (PBS), then reacted for about 30 minutes to an hour at room temperature or near 7° C. in a stain containing X-gal. The tissue samples are then washed in a 1 mM EDTA/PBS solution to stop the β-galactosidase reaction, and staining is observed. mRNA which encodes lacZ can also be detected by ordinary methods.

The compounds or salts thereof obtained by the aforementioned screening method are compounds selected from the test compounds described above which promote or inhibit the activity of a promoter for the DNA of the present invention.

The compounds obtained by this screening method may be in the form of salts. Salts of such compounds, which can be used include salts with physiologically acceptable acids (such as inorganic and organic acids) or bases (such as alkali metals), with physiologically acceptable acid salts being particularly desirable. For example, salts with inorganic acids (such as hydrochloric acid, phosphoric acid, hydrobromic acid or sulphuric acid) or with organic acids (such as acetic acid, formic acid, propionic acid, fumaric acid, maleic acid, succinic acid, tartaric acid, citric acid, malic acid, oxalic acid, benzoic acid, methanesulfonic acid or benzenesulfonic acid) may be used.

Since compounds and salts thereof that promote the activity of a promoter for the DNA of the present invention also promote expression of the protein of the present invention and promote the function of said protein, they are useful as safe and low toxic pharmaceuticals for the prevention of diseases such as cancer (including oral cancer, pharyngeal cancer, lip cancer, tongue cancer, gum cancer, nasopharyngeal cancer, esophageal cancer, stomach cancer, small intestinal cancer, large intestinal cancer (including colon cancer), liver cancer, bile duct cancer, pancreatic cancer, nasal cancer, lung cancer, osteosarcoma, soft tissue cancer, skin cancer, melanocarcinoma, breast cancer, uterine cancer, ovarian cancer, prostate cancer, testicular cancer, penis cancer, bladder cancer, kidney cancer, brain tumors, thyroid cancer, lymphoma, leukemia and other cancers).

On the other hand, because compounds and salts thereof that inhibit the activity of a promoter for the DNA of the present invention also inhibit the expression of the protein of the present invention and inhibit the function of said protein, they are useful as safe and low toxic pharmaceuticals for the treatment of cancer and other diseases, for example.

Compounds derived from compounds obtained by the aforementioned screening method can also be used in the same way.

Drugs comparing a compound or salt thereof obtained by the aforementioned screening method can be manufactured in the same way as the pharmaceuticals comparing the protein or salt thereof of the present invention as described above.

Since preparations obtained in this way are safe and of low toxicity, they can be administered safely to mammals (such as humans, rats, mice, guinea pigs, rabbits, sheep, pigs, cows, horses, cats, dogs, monkeys and the like).

The dosage of the compound or salt thereof depends on the target disease, subject and route of administration, etc., but for example when a compound which inhibits the activity of a promoter for the DNA of the present invention is administered orally for treatment of cancer, the dose is normally about 0.1–100 mg, or preferably about 1.0–50 mg, or more preferably about 1.0–20 mg per day for adults (as 60 kg body weight). In parenteral administration, the single dose of the compound varies depending on the subject, the target disease and so forth. For example, when a compound which inhibits the activity of a promoter for the DNA of the present invention is administered for treatment of cancer in the form of an injection, it is advantageous to administer, for example, a daily dose of about 0.01–30 mg, or preferably about 0.1–20 mg, or more preferably about 0.1–10 mg for adults (as 60 kg body weight) by intravenous injection. For other animal species, the corresponding dose as converted per 60 kg weight can be administered.

On the other hand, when a compound which promotes the activity of a promoter for the DNA of the present invention is administered orally for prevention of cancer, the dose is normally about 0.1–100 mg, or preferably about 1.0–50 mg, or more preferably about 1.0–20 mg per day for adults (as 60 kg body weight). In parenteral administration, the single dose of the compound varies depending on the subject, the target disease and so forth, but for example when a compound which promotes the activity of a promoter for the DNA of the present invention is administered for prevention in the form of an injection, it is advantageous to administer, for example, a daily dose of about 0.01–30 mg, or preferably about 0.1–20 mg, or more preferably about 0.1–10 mg for adults (as 60 kg body weight) by intravenous injection. For other animal species, the corresponding dose as converted per 60 kg weight can be administered.

Thus, non-human mammals which do not express the DNA of the present invention are extremely useful for screening compounds or salts thereof which promote or inhibit the activity of promoters for the DNA of the present invention, and could contribute greatly to discovering the causes of various diseases stemming from failure to express the DNA of the present invention, and to the development of pharmaceuticals for the prevention and treatment of such diseases.

Abbreviations used to describe bases, amino acids and the like in the present Specification and Drawings are based on the abbreviations of the IUPAC-IUB Commission on Biochemical Nomenclature, or on abbreviations in common use in the field. Examples are given below. When an amino acid can have optical isomers, the L form is indicated unless otherwise stated.

| | |
|---|---|
| DNA | Deoxyribonucleic acid |
| cDNA | Complementary deoxyribonucleic acid |
| A | Adenine |
| T | Thymine |
| G | Guanine |
| C | Cytosine |
| Y | Thymine or Cytosine |
| N | Thymine, cytosine, adenine or guanine |
| R | Adenine or guanine |
| M | Cytosine or adenine |
| W | Thymine or adenine |
| S | Cytosine or guanine |
| RNA | Ribonucleic acid |
| mRNA | Messenger ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| ADP | Adenosine diphosphate |
| CDP | Cytidine diphosphate |
| GDP | Guanosine diphosphate |
| EDTA | Ethylene diamine tetra-acetic acid |
| SDS | Sodium dodecyl sulfate |
| EIA | Enzyme immunoassay |
| Gly or G | Glycine |
| Ala or A | Alanine |
| Val or V | Valine |
| Leu or L | Leucine |
| Ile or I | Isoleucine |
| Ser or S | Serine |
| Thr or T | Threonine |
| Cys or C | Cysteine |
| Net or M | Methionine |
| Glu or E | Glutamic acid |
| Asp or D | Aspartic acid |
| Lys or K | Lysine |
| Arg or R | Arginine |
| His or H | Histidine |
| Phe or F | Phenylalanine |
| Tyr or Y | Tyrosine |
| Trp or W | Tryptophan |
| Pro or P | Proline |
| Asn or N | Asparagine |
| Gln or Q | Glutamine |
| pGlu | Pyroglutamic acid |
| Xaa | Unidentified amino acid |

Substitutional groups, protective groups and reagents which appear frequently in this Specification are abbreviated as follows.

| Me | Methyl group |
|---|---|
| Et | Ethyl group |
| Bu | Butyl group |
| Ph | Phenyl group |
| TC | Thiazolidine-4(R)-carboxamide group |
| Tos | p-Toluenesulfonyl |
| CHO | Formyl |
| Bzl | Benzyl |
| Cl₂Bzl | 2,6-Dichlorobenzyl |
| Bom | Benzyloxymethyl |
| Z | Benzyloxycarbonyl |
| Cl-Z | 2-Chlorobenzyloxycarbonyl |
| Br-Z | 2-Bromobenzyloxycarbonyl |
| Boc | t-Butyloxycarbonyl |
| DNP | Dinitrophenol |
| Trt | Trityl |
| Bum | t-Butoxymethyl |
| Fmoc | N-9-Fluorenylmethoxycarbonyl |
| HOBt | 1-Hydroxybenztriazol |
| HOOBt | 3,4-dihydro-3-hydroxy-4-oxo-1,2,3-benzotriadine |
| HONB | 1-hydroxy-5-norbornene-2,3-dicarboxyimido |
| DCC | N,N'-dicyclohexylcarbodiimide |
| TFA | Trifluoroacetic acid |
| DIEA | Diisopropylethylamine |

The SEQ ID NOs of the sequence listing in this Specification indicate the following sequences.

[SEQ ID NO: 1]
Indicates the amino acid sequence of the protein of the present invention.

[SEQ ID NO: 2]
Indicates the base sequence (ORF only, 1053 bp) of cDNA encoding the protein of the present invention represented by SEQ ID NO: 1. Derived from human placenta.

[SEQ ID NO: 3]
Indicates the base sequence (includes before and after ORF, 4955 bp) of the human placenta-derived cDNA described in Example 2 below, encoding the protein of the present invention represented by SEQ ID NO: 1.

[SEQ ID NO: 4]
Indicates the base sequence (1081 bp) of a DNA fragment inserted into the pcDNA 3.1(+) described in Example 2. Derived from SW480.

[SEQ ID NO: 5]
Indicates the amino acid sequence of the human-derived R2 described in Example 2.

[SEQ ID NO: 6]
Indicates the base sequence of the Primer 1 used in Example 2.

[SEQ ID NO: 7]
Indicates the base sequence of the Primer 2 used in Example 2.

[SEQ ID NO: 8]
Indicates the base sequence of the Primer 3 used in Example 2.

[SEQ ID NO: 9]
Indicates the base sequence of the Primer 4 used in Example 2.

[SEQ ID NO: 10]
Indicates the base sequence of--the Primer 5 used in Example 2.

[SEQ ID NO: 11]
Indicates the base sequence of the Primer 6 used in Example 2.

[SEQ ID NO: 12]
Indicates the base sequence (ORF only, 1053 bp) of cDNA encoding the protein of the present invention as represented by SEQ ID NO: 1. Derived from SW480.

[SEQ ID NO: 13]
Indicates the sequence of the Primer 7 used in Example 3.

[SEQ ID NO: 14]
Indicates the sequence of the Primer 8 used in Example 3.

The sequences of the oligonucleotides AS3, SE3 and p53AS used in Example 5 below are shown here in that order.

(SEQ ID NO:15)
AS3:    $A_sC_sA_sT_sT_sT_sA_sC_sC_sT_sC_sA_sT_sC_sC_sT$ (SEQ ID NO:16)
SE3:    $A_sG_sG_sA_sT_sG_sA_sG_sG_sT_sA_sA_sA_sT_sG_sT$ (SEQ ID NO:17)
p53AS:  $C_sC_sC_sT_sG_sC_sT_sC_sC_sC_sC_sC_sC_sT_sG_sG_sC_sT_sC_sC$

In all cases, the 5'- and 3'-termini are OH groups.

The "$_s$" above indicates that an S molecule is bound to the P molecule which connects the 3' and 5' positions of the nucleotide (phosphorothioate binding).

The transformant Escherichia coli XL1 Blue MRF/pcDNA 3.1(−)-TP53R2H obtained in Example 2 below was deposited on May 27, 1999 at the Institute for Fermentation Osaka (IFO), 17–85 Juso-Honmachi 2-chome, Yodogawa-ku, Osaka, Japan as Deposit No. IFO16287, and on Jun. 23, 1999 at the National Institute of Bioscience and Human Technology (NIBH), 1–3 Higashi 1-chome, Tsukuba-shi, Ibaraki, Japan as Deposit No. FERM BP-6764.

The present invention is explained in more detail below using examples., but is not limited by these examples. Genetic manipulation methods such as those used for cloning and determining base sequences were in accordance with publicly known methods (such as those described in Molecular Cloning $2^{nd,}$ J. Sambrook et al, Cold Spring Harbor Lab. Press (1989).

EXAMPLE 1

Differential Display Method

The LacSwitch Expression system (Stratagene Co.) was introduced into SW480 large intestinal cancer cell line lacking normal p53, and a cell line (SW480WTp53) in which expression of normal exogenous p53 could be controlled with isopropyl beta-D-thiogalactopyranoside was established. A cell line (SW480MTp53) in which expression of modified p53 could be controlled was also established as a control. 0, 8, 16, 24, 32 and 40 hours after addition of isopropyl beta-D-thiogalactopyranoside, m-RNA was extracted from these cell lines, and cDNA synthesized using anchor primer {(GT15MC) M:mixture of G,A, and C}. Using these as templates, PCR was performed with a combination of anchor primer {(GT15MC) M:mixture of G,A, and C} and 28 types of arbitrary primer (12mer) labeled with $^{32}P$, the bands were separated by electrophoresis, and the band patterns detected by autoradiography. Since the results showed a novel p53 target gene fragment (cDNA fragment) expression of which increases with induction of normal p53 expression, this band was excised and the cDNA fragment was extracted, and 2$^{nd}$ PCR and 3$^{rd}$ PCR performed under the same conditions as 1$^{st}$ PCR. Following 3$^{rd}$ PCR, the cDNA fragment was ligated with pT7 Blue T vector (Novagen Co.), and the resulting plasmid DNA was introduced into E. coli XL1 Blue MRF using an electroporation unit (Biorad Co.) to produce transformants (clones). Five clones were selected at random from these transformants and the plasmids were purified, and the base sequence of the inserted portion was determined with a sequencer (Applied Biosystem Co., ABI377).

EXAMPLE 2

Isolation of the TP53R2H Gene

An EST search was performed on the sequence obtained in Example 1, and Primers 1 and 2 were prepared based on the extended sequence. mRNA was extracted from the SW480WTp53 0, 8, 16, 24, 32 and 40 hours after addition of isopropyl β-D-thiogalactopyranoside, RT-PCR was performed using cDNA synthesized with oligo (dT) 12–18 primer as the template, an induction of TP53R2H expression was confirmed. Induction of expression of this cDNA fragment was also confirmed in Northern blot analysis (aforementioned m-RNA sample) using a probe prepared from the aforementioned PCR product, and the transcription product was confirmed to be about 5.5 kb in size. The same probe was used to screen a human skeletal muscle derived cDNA library (10$^6$ plaques), resulting in a 4368 bp cDNA fragment. The 5' end was extended by the 5' RACE method using a Marathon cDNA Amplification Kit (Clontech). The template for the extension reaction was cDNA prepared from human placenta mRNA (Clontech) using a Marathon cDNA Amplication Kit (Clontech). 1$^{st}$ PCR was performed using Primer 3 and Primer AP1 (part of the aforementioned Marathon cDNA Amplification Kit), and 2$^{nd}$ PCR using Primer 4 and Primer AP2 (part of the aforementioned Marathon cDNA Amplification Kit), resulting in a cDNA fragment with a base sequence of 4955 bp including 587 bp extension of the 5' end. A 1053 bp ORF (Open Reading Frame) encoding 351 amino acids was discovered in this 4955 bp cDNA sequence (FIGS. 1A–1C ). A homology search of this amino acid sequence revealed that the amino acid sequence had about 80% homology with the small subunit (R2) of human-derived ribonucleotide reductase (FIG. 2).

Of the resulting 4955 bp base sequence, the cDNA fragment with the 1053 bp ORF was cloned into E. coli by the following procedures to obtain transformant Escherichia coli XL1 Blue MRF/pcDNA 3.1(+)-TP53R2H. First, Primer 5 and Primer 6, each complementary to the 1053 bp base sequence but with different restriction enzyme recognition sites (Eco RI and Xho I), were synthesized by publicly known methods. Using Primer 5 and Primer 6, and with cDNA prepared from SW480WTp53 mRNA 40 hours after addition of isopropyl beta-D-thiogalactopyranoside as the template, an RT-PCR reaction was performed to obtain a PCR amplified fragment. This was cut with Eco RI and Xho I and inserted into a site of plasmid vector pcDNA3.1(+) cut with the same restriction enzyme to obtain plasmid pcDNA 3.1(+)-TP53R2H. The resulting plasmid pcDNA 3.1(+)-TP53R2H was introduced into E. coli XL1 Blue MRF to obtain transformant E. coli XL1 Blue MRF/pcDNA 3.1(+)-TP53R2H.

EXAMPLE 3

Confirmation of Induction of p53-Dependent TP53R2H Expression by DNA Damage

Normal human NHDF fibroblasts with normal p53 and MCF7 breast cancer cells with normal p53 and SW480 large intestinal cancer cells lacking normal p53 and H12299 lung cancer cells lacking normal p53 were propagated 1×10$^6$ at a time on 10 cm petri dishes, and DNA damaged (14 Gy γ-ray irradiation) after 24 hours. 0, 6, 12, 24 and 48 hours after γ-ray irradiation the cells were collected, mRNA was extracted, and cDNA was prepared by a reverse transcriptase reaction using oligo (dT) as the primer. With this as the template, changes over time in expression of TP53R2H were examined by RT-PCR using Primer 1 and Primer 2, and changes over time in expression of R2 using Primer 7 and Primer 8.

The results showed almost no expression of TP53R2H in SW480 and H1299, with expression increasing over time only in NHDF and MCF7. Expression of R2 did not change in SW480 and H1299, but decreased over time in NHDF and MCF7 (FIG. 3).

EXAMPLE 4

DNA Repair Test Through Ribonucleotide Reductase Activity During Induction of TP53R2H Expression DNA repair activity through ribonucleotide reductase activity was measured by converting [$^3$H]-CDP to [$^3$H]-dCTP through ribonucleotide reductase in cells, in which the DNA had been damaged, and measuring the radioactivity of [$^3$H]-dCTP in the damaged DNA.

1×10$^6$ MCF7 cells were propagated on 10 cm petri dishes, cellular DNA was damaged (14 Gy γ-ray irradiation) 24 hours later, and after 0, 6, 24 and 48 hours the cells were harvested. After washing the cells with Solution A (150 mM sucrose, 80 mM KCl, 35 mM Hepes (pH 7.4), 5 mM potassium phosphate (pH 7.4), 5 mM MgCl$_2$, 0.5 mM CaCl$_2$), these cells were treated for 1 minute at 4° C. with Solution A containing 0.25 mg/ml lysolecithin. 5×10$^5$ cells were taken from the treated cells, and 300 μl of Solution B (50 mM Hepes (pH 7.4), 10 mM MgCl$_2$, 8 mM dithiothreitol, 0.06 mM FeCl$_3$, 7.5 mM potassium phosphate (pH 7.4), 0.75 mM CaCl$_2$, 10 mM phosphoenol pyruvate, 0.2 mM [$^3$H]-CDP, 0.2 mM GDP, 0.2 mM ADP, 0.2 mM dTDP, 2 mM ATP) was added and reacted for 10 minutes at 37° C. 60 μl of Solution C (60% percholic acid, 0.1% sodium pyrophosphate) was added to the reaction mixture, which was then incubated for 15 minutes on ice and centrifuged at 7000 rpm after addition of 1 ml distilled water to obtained DNA. 100 μl of 0.2N NaOH was added to this DNA, which was then incubated for 30 minutes at 37° C., incubated for a further 15 minutes on ice after addition of 20 μl of Solution C, and centrifuged repeatedly. 75 μl of 0.2N NaOH was added to the DNA obtained, which was then incubated for 30 minutes at 37° C. and mixed with 5 ml of AQUASOL-2 (Packard), and radioactivity was measured with an Aloka LSC-5100 liquid scintillation counter.

Figure 4:
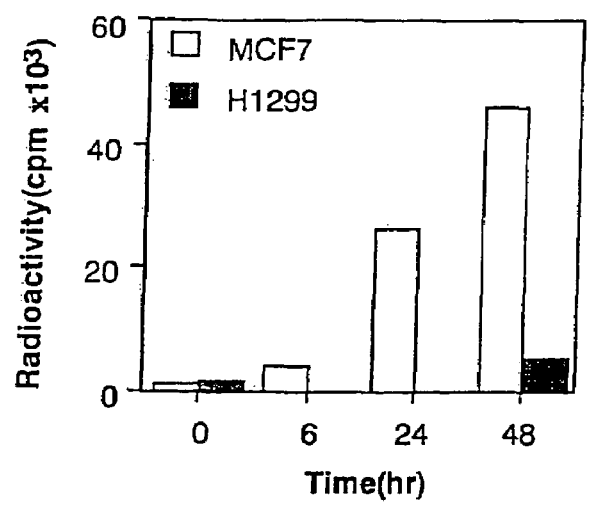
FIG. 4 shows DNA repair activity through ribonucleotide reductase activity during induction of expression of the TP53R2H obtained in Example 4.

In MCF7, the results confirmed an increase in DNA repair activity over time after DNA damage when induction of TP53R2H was confirmed in Example 3. When the same experiment was performed using H1299 which lacked normal p53 and in which TP53R2H expression was not induced, there was only a slight rise in DNA repair activity (FIG. 4)

EXAMPLE 5

TP53R2H Suppression Experiment Using Antisense Oligonucleotides

DNA repair activity through ribonucleotide reductase activity was investigated when TP53R2H expression was suppressed with antisense oligonucleotides.

$2\times10^6$ MCF7 cells were propagated on 10 cm petri dishes, and after 24 hours a TP53R2H antisense oligonucleotide (AS3) a sense oligonucleotide (SE3) and a p53 antisense oligonucleotide (p53AS) were introduced according to attached protocol using a lipofectin reagent (GIBCO BRL). 4 hours later the cellular DNA was damaged (14 Gy γ-ray irradiation), and cells were collected after 0, 24 and 48 hours. DNA repair activity was then measured in the same way as in Example 4 above.

Figure 5:
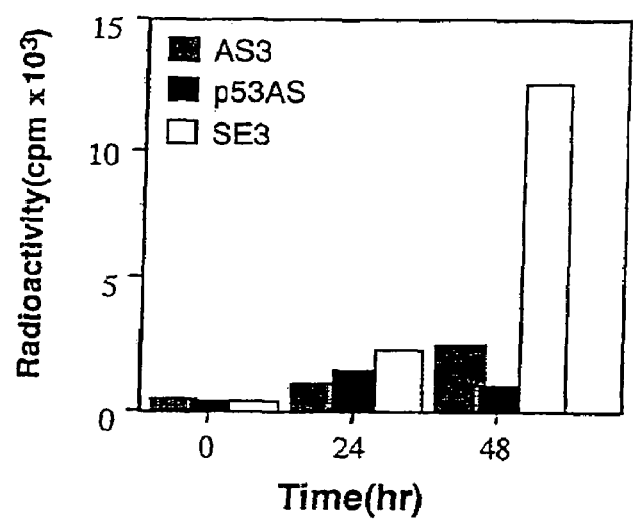
FIG. 5 shows DNA repair activity through ribonucleotide reductase activity when TP53R2H expression was suppressed by using the antisense oligonucleotide obtained in Example 5.

The results confirmed that DNA repair activity declined when TP53R2H expression was suppressed with an antisense oligonucleotide (AS3). DNA repair activity also declined when p53 expression was suppressed with a p53 antisense oligonucleotide (p53AS) (FIG. 5).

Short-term and long-term cell survival rates were also measured when TP53R2H expression was suppressed with an antisense oligonucleotide and DNA was damaged.

$2\times10^6$ MCF7 cells) were propagated on 10 cm Petri dishes, and after 24 hours a p53R2 antisense oligonucleotide (AS3), a sense oligonucleotide (SE3) and a p53 antisense oligonucleotide (p53AS) were introduced using a lipofectin reagent. 4 hours later the cellular DNA was damaged (3 or 14 Gy γ-ray irradiation, adiamycin 0.2 μg/ml, UV 10 J/m²).

In order to study short-term cell survival, the cells were stripped immediately after DNA damage and re-propagated on 6-hole plates to a density of $3\times10^5$, and cell numbers were counted every day for 6 days. To study long-term cell survival, the cells were re-propagated after DNA damage on 10 cm plates to a density of $1\times10^4$ or $1\times10^3$, and the number of colonies 1 mm or more in diameter was counted after three weeks and expressed as a percentage.

Figure 6C:
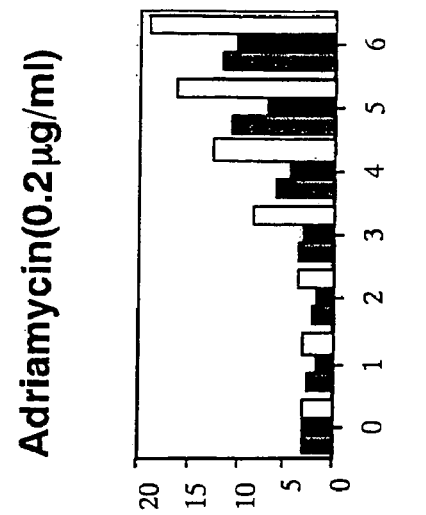
FIG. 6 shows the short-term cell survival rate when TP53R2H activity was suppressed by using the antisense oligonucleotide obtained in Example 5, and the DNA damage was given.
Figure 6B:
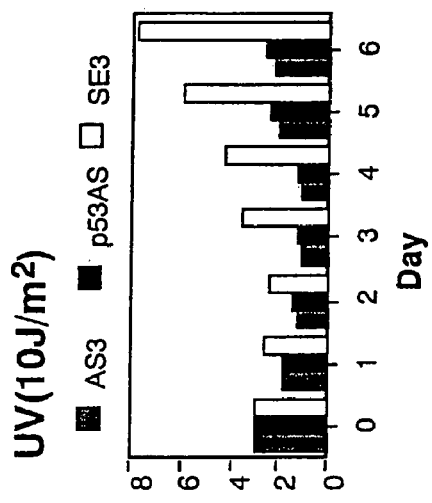
Figure 6A:
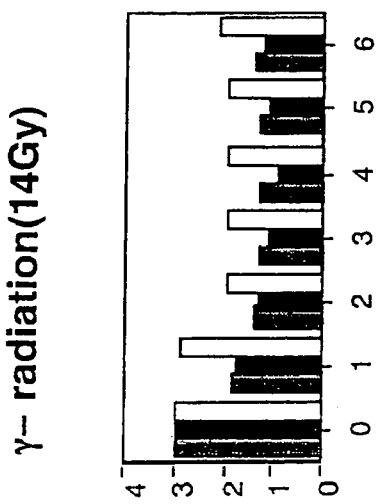

The results confirmed that in both the short- and long-term, when TP53R2H expression is suppressed with an antisense oligonucleotide (AS3), sensitivity to DNA damage increases and cell death is more likely. Similar results were observed using the p53 antisense oligonucleotide (p53AS) (Table 1 and FIG. 6).

Table 1 below shows long-term cell survival when TP53R2H expression was suppressed using the antisense oligonucleotide obtained in Example 5, and DNA was damaged.

TABLE 1

|  | γ-radiation (3Gy) | UV (10 J/m2) | Adriamycin (0.2 μg/ml) |
| --- | --- | --- | --- |
| SE3 | 100% | 100% | 100% |
| AS3 | 59% | 22% | 16% |
| P53AS | 15% | 11% | 10% |

EXAMPLE 6

Cytopathy Experiment Using a Stable Transformant of TP53R2H

Affects on DNA damage were investigated when a stable transformant of TP53R2H was prepared using H1299 to produce strong TP53R2H expression.

pcDNA 3.1(+)-TP53R2H or pcDNA 3.1(+) was introduced into $1\times10^6$ H1299 cells according to attached protocol using TransIT-LT1 (Mirus), and cell lines with introduced TP53R2H or pcDNA 3.1(+) were selected with Geneticin (GIBCO BRL). These cell lines were DMA damaged (adriamycin 0.2 μg/ml), and cells were collected after 0 and 48 hours. The collected cells were washed with PBS and fixed with 70% ethanol, the DNA was stained with propidium iodide, and FACScan was performed according to ordinary methods.

Figures 7A, 7B, 7C, 7D:
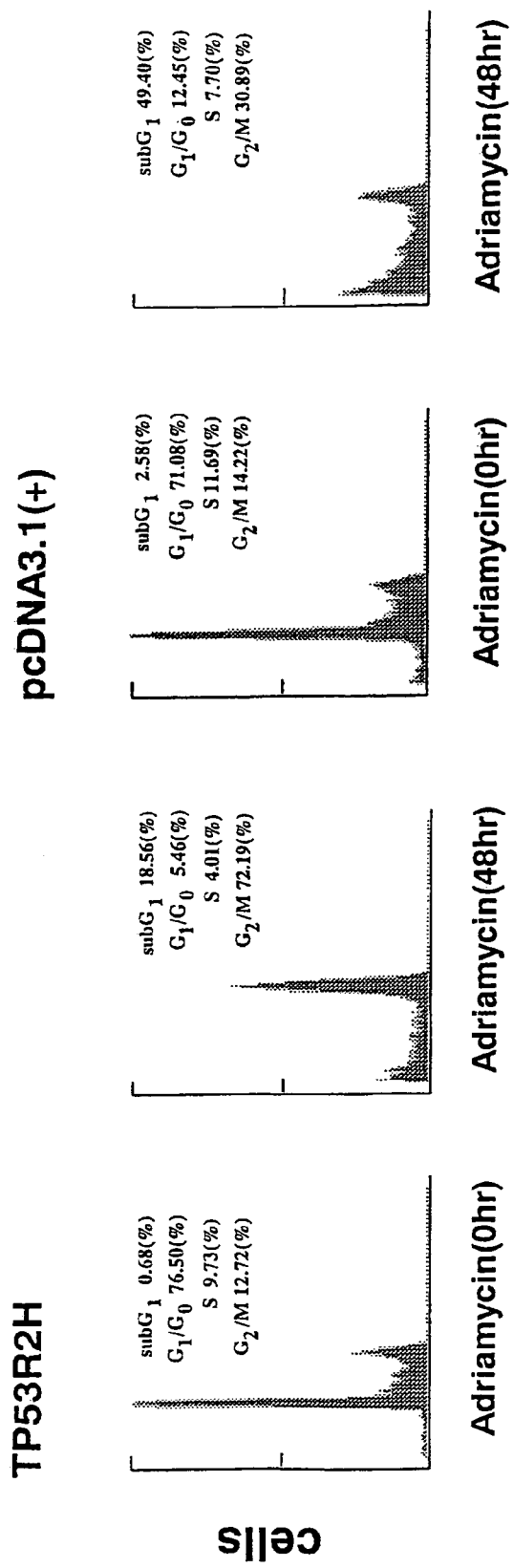
FIG. 7 shows the effect on DNA damage when the stable transformant of TP53R2H obtained in Example 6 was prepared and TP53R2H strongly expressed.

The results confirmed that in H1299 which strongly express TP53R2H, sensitivity to DNA damage (adriamycin 0.2 μg/ml) is reduced and cell death suppressed (G2/M arrest occurs) (FIG. 7).

INDUSTRIAL APPLICABILITY

Because the protein, partial peptide thereof and salts of these of the present invention have enzyme activity which catalyzes ribonucleotide reductase and other enzyme metabolism, the protein, partial peptide thereof and salts of these of the present invention, and DNA encoding the protein or part of the protein of the present invention are useful as pharmaceuticals for treatment and prevention of diseases such as cancer, for example. Moreover, b cause the DNA of the present invention can detect abnormalities of expression of the DNA of the present invention, it is useful as a genetic diagnostic for diseases such as cancer.

Because antibodies to the protein, partial peptide thereof and salts of these of the present invention can specifically recognize the protein, partial peptide thereof and salts of these of the present invention, they are useful in quantifying the protein, etc. of the present invention in a test solution.

Moreover, the protein, partial peptide thereof and salts of these of the present invention are useful as reagents for screening compounds or salts thereof which promote or inhibit the activity of the protein of the present invention.

What is claimed is:

1. An isolated nucleic acid molecule comprising a base sequence encoding a protein having the amino acid sequence set forth as SEQ ID NO: 1 and having ribonucleotide reductase activity.

2. The isolated nucleic acid molecule according to claim 1, wherein the molecule is DNA.

3. The isolated nucleic acid molecule according to claim 2, wherein the molecule comprises the base sequence set forth as SEQ ID NO: 2.

4. The isolated nucleic acid molecule according to claim 2, wherein the molecule comprises the base sequence set forth as SEQ ID NO: 12.

5. A recombinant vector comprising the nucleic acid molecule according to claim 1.

6. A pharmaceutical composition comprising the nucleic acid molecule according to claim 1 and a pharmaceutically acceptable carier.

* * * * *

SEQUENCE LISTING

```
<160> NUMBER OF SEQ ID NOS: 14

<210> SEQ ID NO 1
<211> LENGTH: 351
<212> TYPE: PRT
<213> ORGANISM: Homo sapiens
<220> FEATURE:
<223> OTHER INFORMATION:
```

<400> SEQUENCE: 1

```
Met Gly Asp Pro Glu Arg Pro Glu Ala Ala Gly Leu Asp Gln Asp Glu
 1               5                  10                  15

Arg Ser Ser Asp Thr Asn Glu Ser Glu Ile Lys Ser Asn Glu Glu
                20                  25                  30

Pro Leu Leu Arg Lys Ser Ser Arg Arg Phe Val Ile Phe Pro Ile Gln
                35                  40                  45

Tyr Pro Asp Ile Trp Lys Met Tyr Lys Gln Ala Gln Ala Ser Phe Trp
 50                  55                  60

Thr Ala Glu Glu Val Asp Leu Ser Lys Asp Leu Pro His Trp Asn Lys
 65                  70                  75                  80

Leu Lys Ala Asp Glu Lys Tyr Phe Ile Ser His Ile Leu Ala Phe Phe
                85                  90                  95

Ala Ala Ser Asp Gly Ile Val Asn Glu Asn Leu Val Glu Arg Phe Ser
                100                 105                 110

Gln Glu Val Gln Val Pro Glu Ala Arg Cys Phe Tyr Gly Phe Gln Ile
                115                 120                 125

Leu Ile Glu Asn Val His Ser Glu Met Tyr Ser Leu Leu Ile Asp Thr
 130                 135                 140

Tyr Ile Arg Asp Pro Lys Lys Arg Glu Phe Leu Phe Asn Ala Ile Glu
145                 150                 155                 160

Thr Met Pro Tyr Val Lys Lys Ala Asp Trp Ala Leu Arg Trp Ile
                165                 170                 175

Ala Asp Arg Lys Ser Thr Phe Gly Glu Arg Val Val Ala Phe Ala Ala
                180                 185                 190

Val Glu Gly Val Phe Phe Ser Gly Ser Phe Ala Ala Ile Phe Trp Leu
                195                 200                 205

Lys Lys Arg Gly Leu Met Pro Gly Leu Thr Phe Ser Asn Glu Leu Ile
 210                 215                 220

Ser Arg Asp Glu Gly Leu His Cys Asp Phe Ala Cys Leu Met Phe Gln
225                 230                 235                 240

Tyr Leu Val Asn Lys Pro Ser Glu Glu Arg Val Arg Glu Ile Ile Val
                245                 250                 255

Asp Ala Val Lys Ile Glu Gln Glu Phe Leu Thr Glu Ala Leu Pro Val
                260                 265                 270

Gly Leu Ile Gly Met Asn Cys Ile Leu Met Lys Gln Tyr Ile Glu Phe
                275                 280                 285

Val Ala Asp Arg Leu Leu Val Glu Leu Gly Phe Ser Lys Val Phe Gln
                290                 295                 300

Ala Glu Asn Pro Phe Asp Phe Met Glu Asn Ile Ser Leu Glu Gly Lys
305                 310                 315                 320

Thr Asn Phe Phe Glu Lys Arg Val Ser Glu Tyr Gln Arg Phe Ala Val
                325                 330                 335

Met Ala Glu Thr Thr Asp Asn Val Phe Thr Leu Asp Ala Asp Phe
                340                 345                 350

<210> SEQ ID NO 2
<211> LENGTH: 1053
<212> TYPE: DNA
<213> ORGANISM: Homo sapiens
<220> FEATURE:
<223> OTHER INFORMATION:

<400> SEQUENCE: 2
```

```
atgggcgacc cggaaaggcc ggaagcggcc gggctggatc aggatgagag atcatcttca    60
gacaccaacg aaagtgaaat aaagtcaaat gaagagccac tcctaagaaa gagttctcgc   120
cggtttgtca tctttccaat ccagtaccct gatatttgga aaatgtataa acaggcacag   180
gcttccttct ggacagcaga agaggtcgac ttatcaaagg atctccctca ctggaacaag   240
cttaaagcag atgagaagta cttcatctct cacatcttag cctttttttgc agccagtgat   300 ggaattgtaa atgaaaattt ggtggagcgc tttagtcagg aggtgcaggt tccagaggct   360
cgctgtttct atggctttca aattctcatc gagaatgttc actcagagat gtacagtttg   420
ctgatagaca cttacatcag atcccaag aaaagggaat ttttatttaa tgcaattgaa   480
accatgccct atgttaagaa aaagcagat tgggccttgc gatggatagc agatagaaaa   540
tctacttttg gggaaagagt ggtggccttt gctgctgtag aaggagttt cttctcagga   600 tcttttgctg ctatattctg gctaaagaag agaggtctta tgccaggact cactttttcc   660
aatgaactca tcagcagaga tgaaggactt cactgtgact ttgcttgcct gatgttccaa   720
tacttagtaa ataagccttc agaagaaagg gtcagggaga tcattgttga tgctgtcaaa   780
attgagcagg agttttttaac agaagccttg ccagttggcc tcattggaat gaattgcatt   840
ttgatgaaac agtacattga gtttgtagct gacagattac ttgtggaact tggattctca   900
aaggtttttc aggcagaaaa tccttttgat tttatgaaa acatttcttt agaaggaaaa   960
acaaatttct ttgagaaacg agtttcagag tatcagcgtt ttgcagttat ggcagaaacc  1020
acagataacg tcttcacctt ggatgcagat ttt                              1053

<210> SEQ ID NO 3
<211> LENGTH: 4955
<212> TYPE: DNA
<213> ORGANISM: Homo sapiens
<220> FEATURE:
<223> OTHER INFORMATION:

<400> SEQUENCE: 3
ggctggccga agttaggcgg agccccgagg cggggaggc ggggccgggc cggcgcaggg    60
agagtcactc aatggacagg cgagaaagca ggaccggcgc ggcggggcgg ggccggccga   120
gtccctagag ctggggcgg ggcggaccca gcggaccagc ggaccacctg ggtgctgtcg   180
tagttggagg tggcctgagg agctcagttc cctcagcgcc cgtagcttcg gcggagtctg   240
cgcgatgggc gacccggaaa ggccggaagc ggccgggctg gatcaggatg agagatcatc   300
ttcagacacc aacgaaagtg aaataaagtc aaatgaagag ccactcctaa gaaagagttc   360
tcgccggttt gtcatctttc caatccagta ccctgatatt tggaaaatgt ataaacaggc   420
acaggcttcc ttctggacag cagaagaggt cgacttatca aaggatctcc ctcactggaa   480
caagcttaaa gcagatgaga agtacttcat ctctcacatc ttagcctttt ttgcagccag   540
tgatggaatt gtaaatgaaa atttggtgga gcgctttagt caggaggtgc aggttccaga   600
ggctcgctgt ttctatggct ttcaaattct catcgagaat gttcactcag agatgtacag   660
tttgctgata gacacttaca tcagagatcc aagaaaagg gaatttttat ttaatgcaat   720
tgaaaccatg ccctatgtta agaaaaagc agattgggcc ttgcgatgga tagcagatag   780
aaaatctact tttggggaaa gagtggtggc ctttgctgct gtagaaggag ttttcttctc   840
aggatctttt gctgctatat tctggctaaa gaagagaggt cttatgccag gactcacttt   900
ttccaatgaa ctcatcagca gagatgaagg acttcactgt gactttgctt gcctgatgtt   960
ccaatactta gtaaataagc cttcagaaga aagggtcagg gagatcattg ttgatgctgt  1020
```

-continued

```
caaaattgag caggagtttt taacagaagc cttgccagtt ggcctcattg gaatgaattg    1080
cattttgatg aaacagtaca ttgagtttgt agctgacaga ttacttgtgg aacttggatt    1140
ctcaaaggtt tttcaggcag aaaatccttt tgattttatg gaaaacattt ctttagaagg    1200
aaaaacaaat ttctttgaga aacgagtttc agagtatcag cgttttgcag ttatggcaga    1260
aaccacagat aacgtcttca ccttggatgc agattttaa aaaacctctc gtttaaaac     1320
tctataaact tgtcattggt aaatagtagt ctattttcct ctgcttaaaa aaaattttaa    1380
gtatatcctt taaaggactg ggggtttgct caaaaggaaa tccaaaacct attctaaaca    1440
atttgcattt atataatttt cctgtttaac aacaagagtg tgacctaaat gcttttgtct    1500
tgtcactgaa ataaagatg gcattatgtg gttaagagca tggggcgagg ggtcagacat     1560
gagtctaagg ttctgcccct actccagtgt gtgacccttg gcaagtcagt taatcttggt    1620
aaacctcggt gtacttatct ttaaaatggg agtaatagta ggtcctaaat tcatagagtg    1680
gatattagga ttaggatgca aaaataaatg cttaaccaac actactactg ttagcaccac    1740
tactaattat cattcattga taatattaat tgcaatgatg ttgtaataaa atactctcat    1800
ttccttaaaa taattgtgat tctaggtcct aggatctaga attagatctt tgtattttta    1860
atgcttaggg gaagaatata agtatctcct taaaagaac ataattctca ttcacgcaag     1920
aataagttct ttgaattcct tagtatgtag tgaagaaaat ttagttgtta gttgctttgg    1980
gaagcctact tatggagtgg aaaccaggag gttatcatgg tagttgacct tgtaagaaaa    2040
atgattcttc ttcagaaatt aaaaacataa ctattgccag atttagctct ggaatgttta    2100
gaatcaggct agaatagcat tttccaaaga atattctaag agctattagc tcctctagat    2160
attttgttgg gggaaaaagg ggattctgtg gtcagatgag tttgggaaat gctgaacact    2220
tcattcttct ttagcaagta cagtcagtac atcaaagact gagcagttca gtggtacata    2280
aatttatctc gccctgcata ttcccaacat acttaacaca gatgttttt acctgttaac     2340
atctcaccca gctagtgttc ctcagaacaa agattggaaa agctggccg agaaccattt     2400
atacatagag gaagggctta cggactgaga aaggagaac atggtaggga ttattgaatc     2460
atttcaaatt tataccaagc ctgaatagtg taccagcaat tgacttaggc tgtgtttctt    2520
tatggtttta aaactcttga gctgttataa gagatagttc ttttaatgtg actatgcaac    2580
atgatagcca atggtgaggg aaaaggaggt ttctctagaa gagtctgatg aaaggccggg    2640
aaccaaggtt tttgagaagt ctgcccctat ttatttttag taagtatcaa gaggtagcct    2700
gagcctagtt agagttagac ctgtctttgg atgaagaagt cttaatactg aaatactgaa    2760
tttttaatac attattattt ggtattctgt atacccttc aagcagttgt ttcccattcc     2820
caacaaactg tactttatac aattctggat gctaaaactt agagattttc tctttgcata    2880
aattttggct ccattctttc cataacaatc taatcaaaac tgggagttct caagtgaatg    2940
caaaaggagc aggccataac tttatttgtt agagacactg tcagaaactt gagatctttt    3000
ggcctatgat aataccatta attttttgcat tgcttcagtt tgccaagtgt ttttacatca    3060
tctcatttga tctcaaaaca gcttgacaga gcaactgtta ttgaaatatt acagatggaa    3120
agaatgaggc tcagggaagt taaatgactt ggccaagatc tgctcatcgt cactgtctgt    3180
acagtatttt tttttagagg ttgtaatgtc tcagatttag tcctttacca tctatgttga    3240
tttgcttttg tctatttcct cattaattga atatacttta aatatatata ttaaagtatc    3300
aaaatataga gagacatttg aactgtattc aggtaatatg tttaaagata tttatatatt    3360
```

-continued

```
gccatacaaa aacttaacat ttaaaactga taatatctgt aatgacatca gaatgaaaga    3420
aaaaaaattg tacagtgtat attcctttgt tttgaatcca aatctttttc ataggtaatg    3480
acagatgcct taatgtgaag cttatttata atagcaataa acctaactgg atttggatga    3540
agaagtctta atactgacat actggatttt taatgcactg gtttgttatt tggtattcta    3600
tctctttttc caggcctcca ggttgcacat ttatttatta tgttcaatac tttggttctt    3660
agttcttaaa gaatcaagaa gttgtgtaat cttttaaaaa tattatcttg cagataaaga    3720
aaaaaattaa gagtgtgttt acaactgttt tctcttttt acagtacatg tatttaaatc    3780
attgctataa taaagttaag ttcattagga atataaaaac ttgcagttct atgatagatt    3840
gcatttatta aaaatgtttc attgtatcac atagaaatat ggccaggaag acttgagaa    3900 gacagtttga tccattgctt ttagacagga ctgggttttg ctgtccaatt atatacaata    3960 atagttttc ttacaactaa gctggcccca gccttgtctt gatattaata catgaaattt    4020
ttataattgt ctcattgtct catttagaaa catccatatt tttctgcttt ttctattgcc    4080
attttttatt tgtgcatgaa ttgattattg agaaaatgta gcagtttgca tatttaaaaa    4140
ttaatcattt tgcatttac atttaaatat gctaacatcg ctgtcataga attcccaaat    4200
ttcatttgta gatactgaac taagggctaa tgtcaggagc tgatttttaa tgataaagct    4260
gcagatgggc taaataaaag ccaaattaat cctacaatca ggtattatgt ttttaaacca    4320
agttgagtga attggtagtg gacttgggaa atcttcccca gcagaatctg gatgaatggc    4380
acagaattga aatctctttg tttcccacca tttccctta gtgctctgc tcctttgtaa    4440 aaagttaaag atttgaaaga aatctcata ttcccgaggc attaggaaga aaggatttaa    4500
tcccttcaat ttggggctta atcttgttta aaaaaatgta agtgaagatg gaaggctgga    4560
gagaatgatt gcttttgta cagttaaata aggtcacaat attcttacat actttgtttt    4620
acaactgtgt tttcattttt tcaaatgtct ggccatttag caaagttatt tactatttac    4680
tgtgtacata gaaaggttta ttatgtgtgg tgtatctaaa ttttttttg ctgaaataca    4740 ttatggtcaa tcaagccaag cctgcatgta cagaatttgt ttttttttca aataaattag    4800
ttgttttctt attttttgg cttagtatgt tgaaataaac tatggtatct tcatcatttt    4860
gtacatttcc tttttgagga aggtttcttt ataagtgcaa gggctaccct aataaaggaa    4920
tgtatatact tacaaaaaaa aaaaaaaaaa aaaaa                                4955
```

<210> SEQ ID NO 4
<211> LENGTH: 1081
<212> TYPE: DNA
<213> ORGANISM: Homo sapiens
<220> FEATURE:
<223> OTHER INFORMATION:

<400> SEQUENCE: 4

```
gaattccaga ccgtgcatca tgggcgaccc ggaaaggccg gaagcggccg ggctggatca      60
ggatgagaga tcatcttcag acaccaacga aagtgaaata aagtcaaatg aagagccact    120
cctaagaaag agttctcgcc ggtttgtcat ctttccaatc cagtaccctg atatttggaa    180
aatgtataaa caggcacagg cttccttctg acagcagaa gaggttgact tatcaaagga    240
tctccctcac tggaacaagc ttaaagcaga tgagaagtac ttcatctctc acatcttagc    300
cttttttgca gccagtgatg gaattgtaaa tgaaaatttg gtggagcgct ttagtcagga    360
ggtgcaggtt ccagaggctc gctgtttcta tggctttcaa attctcatcg agaatgttca    420
ctcagagatg tacagtttgc tgatagacac ttacatcaga gatcccaaga aagggaatt    480
```

```
tttatttaat gcaattgaaa ccatgcccta tgttaagaaa aaagcagatt gggccttgcg      540
atggatagca gatagaaaat ctacttttgg ggaaagagtg gtggcctttg ctgctgtaga      600
aggagttttc ttctcaggat cttttgctgc tatattctgg ctaaagaaga gaggtcttat      660
gccaggactc acttttcca atgaactcat cagcagagat gaaggacttc actgtgactt       720
tgcttgcctg atgttccaat acttagtaaa taagccttca gaagaaaggg tcagggagat      780
cattgttgat gctgtcaaaa ttgagcagga gttttaaca gaagccttgc cagttggcct       840
cattggaatg aattgcattt tgatgaaaca gtacattgag tttgtagctg acagattact      900
tgtggaactt ggattctcaa aggttttca ggcagaaaat ccttttgatt ttatggaaaa       960
catttcttta aaggaaaaa caaatttctt tgagaaacga gtttcagagt atcagcgttt      1020
tgcagttatg gcagaaacca cagataacgt cttcaccttg gatgcagatt tttaactcga     1080
g                                                                     1081
```

```
<210> SEQ ID NO 5
<211> LENGTH: 389
<212> TYPE: PRT
<213> ORGANISM: Homo sapiens
<220> FEATURE:
<223> OTHER INFORMATION:

<400> SEQUENCE: 5
```

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn
            20                  25                  30

Thr Pro Pro Ala Leu Ser Gly Thr Arg Val Leu Ala Ser Lys Thr Ala
        35                  40                  45

Arg Arg Ile Phe Gln Glu Pro Thr Glu Pro Lys Thr Lys Ala Ala Ala
    50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys
                85                  90                  95

Ala Glu Ala Ser Phe Trp Thr Ala Glu Glu Val Asp Leu Ser Lys Asp
            100                 105                 110

Ile Gln His Trp Glu Ser Leu Lys Pro Glu Glu Arg Tyr Phe Ile Ser
        115                 120                 125

His Val Leu Ala Phe Phe Ala Ala Ser Asp Gly Ile Val Asn Glu Asn
    130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                165                 170                 175

Ser Leu Leu Ile Asp Thr Tyr Ile Lys Asp Pro Lys Glu Arg Glu Phe
            180                 185                 190

Leu Phe Asn Ala Ile Glu Thr Met Pro Cys Val Lys Lys Ala Asp
        195                 200                 205

Trp Ala Leu Arg Trp Ile Gly Asp Lys Glu Ala Thr Tyr Gly Glu Arg
    210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr

```
                245                 250                 255
Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
        275                 280                 285

Val Arg Glu Ile Ile Ile Asn Ala Val Arg Ile Glu Gln Glu Phe Leu
    290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
            325                 330                 335

Phe Ser Lys Val Phe Arg Val Glu Asn Pro Phe Asp Phe Met Glu Asn
        340                 345                 350

Ile Ser Leu Glu Gly Lys Thr Asn Phe Phe Glu Lys Arg Val Gly Glu
    355                 360                 365

Tyr Gln Arg Met Gly Val Met Ser Ser Pro Thr Glu Asn Ser Phe Thr
370                 375                 380

Leu Asp Ala Asp Phe
385

<210> SEQ ID NO 6
<211> LENGTH: 21
<212> TYPE: DNA
<213> ORGANISM: Artificial Sequence
<220> FEATURE:
<223> OTHER INFORMATION:

<400> SEQUENCE: 6
tgaactcatc agcagagatg a                                          21

<210> SEQ ID NO 7
<211> LENGTH: 22
<212> TYPE: DNA
<213> ORGANISM: Artificial Sequence
<220> FEATURE:
<223> OTHER INFORMATION:

<400> SEQUENCE: 7
cctaatccta atatccactc ta                                         22

<210> SEQ ID NO 8
<211> LENGTH: 26
<212> TYPE: DNA
<213> ORGANISM: Artificial Sequence
<220> FEATURE:
<223> OTHER INFORMATION:

<400> SEQUENCE: 8
ttccccaaaa gtagattttc tatctg                                     26

<210> SEQ ID NO 9
<211> LENGTH: 25
<212> TYPE: DNA
<213> ORGANISM: Artificial Sequence
<220> FEATURE:
<223> OTHER INFORMATION:

<400> SEQUENCE: 9
gcaaactgta catctctgag tgaac                                      25

<210> SEQ ID NO 10
```

-continued

```
<211> LENGTH: 43
<212> TYPE: DNA
<213> ORGANISM: Artificial Sequence
<220> FEATURE:
<223> OTHER INFORMATION:

<400> SEQUENCE: 10
ccggaattcc agaccgtgca tcatgggcga cccggaaagg ccg              43

<210> SEQ ID NO 11
<211> LENGTH: 36
<212> TYPE: DNA
<213> ORGANISM: Artificial Sequence
<220> FEATURE:
<223> OTHER INFORMATION:

<400> SEQUENCE: 11
ccgctcgagt taaaaatctg catccaaggt gaagac                       36

<210> SEQ ID NO 12
<211> LENGTH: 1053
<212> TYPE: DNA
<213> ORGANISM: Homo sapiens
<220> FEATURE:
<223> OTHER INFORMATION:

<400> SEQUENCE: 12
atgggcgacc cggaaaggcc ggaagcggcc gggctggatc aggatgagag atcatcttca    60
gacaccaacg aaagtgaaat aaagtcaaat gaagagccac tcctaagaaa gagttctcgc   120
cggtttgtca tctttccaat ccagtaccct gatatttgga aaatgtataa acaggcacag   180
gcttccttct ggacagcaga agaggttgac ttatcaaagg atctccctca ctggaacaag   240
cttaaagcag atgagaagta cttcatctct cacatcttag ccttttttgc agccagtgat   300
ggaattgtaa atgaaaattt ggtggagcgc tttagtcagg aggtgcaggt tccagaggct   360
cgctgtttct atggctttca aattctcatc gagaatgttc actcagagat gtacagtttg   420
ctgatagaca cttacatcag agatcccaag aaaagggaat tttatttaa tgcaattgaa    480 accatgccct atgttaagaa aaaagcagat tgggccttgc gatggatagc agatagaaaa   540 tctactttg gggaaagagt ggtggccttt gctgctgtag aaggagtttt cttctcagga    600
tcttttgctg ctatattctg gctaaagaag agaggtctta tgccaggact cacttttttcc  660 aatgaactca tcagcagaga tgaaggactt cactgtgact tgcttgcct gatgttccaa    720 tacttagtaa ataagccttc agaagaaagg gtcagggaga tcattgttga tgctgtcaaa   780
attgagcagg agtttttaac agaagccttg ccagttggcc tcattggaat gaattgcatt   840
ttgatgaaac agtacattga gtttgtagct gacagattac ttgtggaact tggattctca   900 aaggttttc aggcagaaaa tccttttgat tttatggaaa acatttcttt agaaggaaaa    960
acaaatttct tgagaaacg agtttcagag tatcagcgtt ttgcagttat ggcagaaacc   1020
acagataacg tcttcacctt ggatgcagat ttt                                1053

<210> SEQ ID NO 13
<211> LENGTH: 17
<212> TYPE: DNA
<213> ORGANISM: Artificial Sequence
<220> FEATURE:
<223> OTHER INFORMATION:

<400> SEQUENCE: 13
cgcgtcctgg ccagcaa                                            17
```

```
<210> SEQ ID NO 14
<211> LENGTH: 20
<212> TYPE: DNA
<213> ORGANISM: Artificial Sequence
<220> FEATURE:
<223> OTHER INFORMATION:

<400> SEQUENCE: 14
ccaagtaagg gcacatcttc                                              20
```